(12) United States Patent
Ferguson et al.

(10) Patent No.: US 8,771,944 B2
(45) Date of Patent: *Jul. 8, 2014

(54) USE OF MICRO-RNA AS A BIOMARKER OF IMMUNOMODULATORY DRUG ACTIVITY

(75) Inventors: Gregory D. Ferguson, San Diego, CA (US); Helen Brady, San Diego, CA (US); Kyle Chan, San Diego, CA (US); Normand R. Richard, Ramona, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/104,927

(22) Filed: May 10, 2011

(65) Prior Publication Data
US 2012/0035068 A1    Feb. 9, 2012

Related U.S. Application Data

(63) Continuation of application No. 12/340,472, filed on Dec. 19, 2008, now Pat. No. 7,964,354.

(60) Provisional application No. 61/008,824, filed on Dec. 20, 2007.

(51) Int. Cl.
C12Q 1/68    (2006.01)

(52) U.S. Cl.
USPC ............................................. 435/6.1

(58) Field of Classification Search
USPC ............................................. 435/6.1
See application file for complete search history.

(56) References Cited

U.S. PATENT DOCUMENTS

| | | | |
|---|---|---|---|
| 5,635,517 A | 6/1997 | Muller et al. | |
| 5,698,579 A | 12/1997 | Muller | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,458,810 B1 | 10/2002 | Muller et al. | |
| 6,476,052 B1 | 11/2002 | Muller et al. | |
| 6,555,554 B2 | 4/2003 | Muller et al. | |
| 6,927,024 B2 | 8/2005 | Dodge et al. | |
| 7,091,353 B2 | 8/2006 | Robarge et al. | |
| 7,101,663 B2 | 9/2006 | Godfrey et al. | |
| 7,122,799 B2 | 10/2006 | Hsieh et al. | |
| 7,186,507 B2 | 3/2007 | Bacallao et al. | |
| 7,244,759 B2 | 7/2007 | Muller et al. | |
| 7,465,800 B2 | 12/2008 | Jaworsky et al. | |
| 7,964,354 B2 * | 6/2011 | Ferguson et al. ............ 435/6.11 |
| 2000/3045552 | 3/2003 | Robarge et al. | |
| 2006/0188475 A1 | 8/2006 | Xu et al. | |
| 2006/0205787 A1 | 9/2006 | Muller et al. | |
| 2007/0049618 A1 | 3/2007 | Muller et al. | |
| 2007/0065844 A1 | 3/2007 | Golub et al. | |
| 2007/0232553 A1 * | 10/2007 | Baltimore et al. ............ 514/26 |
| 2008/0182245 A1 | 7/2008 | Brown et al. | |
| 2009/0004209 A1 | 1/2009 | Ruchelman et al. | |
| 2009/0131346 A1 * | 5/2009 | Sorio ............................ 514/44 |
| 2009/0142297 A1 | 6/2009 | Muller et al. | |
| 2009/0280167 A1 * | 11/2009 | Trieu et al. .................... 424/450 |
| 2010/0202973 A1 * | 8/2010 | Pivarcsi et al. ................ 424/9.2 |
| 2010/0298407 A1 * | 11/2010 | Mendell et al. ............ 514/44 A |

FOREIGN PATENT DOCUMENTS

| | | |
|---|---|---|
| EP | 1777301 | 4/2007 |
| WO | 93/18186 | 9/1993 |
| WO | 98/03502 | 1/1998 |
| WO | 98/54170 | 12/1998 |
| WO | 02/059106 | 8/2002 |
| WO | 2005/118806 | 12/2005 |
| WO | 2007/033023 | 3/2007 |
| WO | 2007/073737 | 7/2007 |
| WO | 2007/081740 | 7/2007 |
| WO | 2008/042231 | 4/2008 |
| WO | 2008/079303 | 7/2008 |

OTHER PUBLICATIONS

Babak et al., "Probing microRNAs with microarrays: tissue specificity and functional inference," RNA, 10:1813-1819 (2004).
Bustin et al., "Real-time reverse transcription PCR (qRT-PCR) and its potential use in clinical diagnosis," Clin. Sci., 109:365-379 (2005).
Corral et al., "Immunomodulation by thalidomide and thalidomide analogues," Ann. Rheum. Dis., 58 (suppl I) 1107-1113 (1999).
Gall et al., "Nucleic acid hybridization in cytological preparations," Meth. Enzymol., 21:470-480 (1981).
Kallioniemi et al., "Comparative genomic hybridization for molecular cytogenetic analysis of solid tumors," Science, 258:818-821 (1992).
Liu et al., "An oligonucleotide microchip for genome-wide microRNA profiling in human and mouse tissues," Proc. Natl. Acad. Sci. USA, 101:9740-9744 (2004).
Liu et al., "Patterns of known and novel small RNAs in human cervical cancer," Cancer Res., 67:6031-6043 (2007).
Marriott et al., "Immunotherapeutic and antitumour potential of thalidomide analogues," Expert Opin. Biol. Ther., 1 (4):1-8 (2001).

(Continued)

*Primary Examiner* — Brian Whiteman
(74) *Attorney, Agent, or Firm* — Jones Day

(57) ABSTRACT

Methods of determining the activity of an immunomodulatory compound by measuring the presence of an miRNA in a sample are disclosed. Additionally disclosed are methods of assessing the patient compliance in patients treated with an immunomodulatory compound.

2 Claims, 2 Drawing Sheets

(56) References Cited

OTHER PUBLICATIONS

Moschos et al., "Expression profiling in vivo demonstrates rapid changes in lung microRNA levels following lipopolysaccharide-induced inflammation but not in the anti-inflammatory action of glucocorticoids," BMC Genomics, 8:240-252 (2007).

Muller et al., "Structural modifications of thalidomide produce analogs with enhanced tumor necrosis factor inhibitory activity," J. Med. Chem., 39(17):3238-3240 (1996).

Muller et al., "Thalidomide analogs and PDE4 inhibition.," Bioorg. Med. Chem. Lett., 8:2669-2674 (1998).

Salter et al., "Gene expression signatures of radiation response are specific, durable and accurate in mice and humans," PLoS ONE, 3(4):e1912 (2008).

Thomson et al., "A custom microarray platform for analysis of microRNA gene expression," Nat. Methods, 1:47-53 (2004).

* cited by examiner

SEQUENCE LISTING

<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
cagugcaaug uuaaaagggc au                                          22

<210> SEQ ID NO 2
<211> LENGTH: 22
<212> TYPE: RNA
<213> ORGANISM: Homo sapiens

<400> SEQUENCE: 2
ugagaacuga auuccauagg cu                                          22

<210> SEQ ID NO 3
<211> LENGTH: 21
<212> TYPE: RNA
<213> ORGANISM: Homo spaiens

<400> SEQUENCE: 3
ugagaugaag cacuguagcu c                                           21

<210> SEQ ID NO 4
<211> LENGTH: 23
<212> TYPE: RNA
<213> ORGANISM: Homo sapiens

<400> SEQUENCE: 4
guccaguuuu cccaggaauc ccu                                         23

<210> SEQ ID NO 5
<211> LENGTH: 22
<212> TYPE: RNA
<213> ORGANISM: Homo sapiens

<400> SEQUENCE: 5
cacccguaga accgaccuug cg                                          22

<210> SEQ ID NO 6
<211> LENGTH: 24
<212> TYPE: RNA
<213> ORGANISM: Homo sapiens

<400> SEQUENCE: 6
ucccugagac ccuuuaaccu guga                                        24

<210> SEQ ID NO 7
<211> LENGTH: 22
<212> TYPE: RNA
<213> ORGANISM: Homo sapiens

<400> SEQUENCE: 7
uucccuuugu cauccuaugc cu                                          22

<210> SEQ ID NO 8
<211> LENGTH: 21
<212> TYPE: RNA
<213> ORGANISM: Homo sapiens

<400> SEQUENCE: 8

```
caaaacguga ggcgcugcua u                                             21

<210> SEQ ID NO 9
<211> LENGTH: 23
<212> TYPE: RNA
<213> ORGANISM: Homo spaiens

<400> SEQUENCE: 9
uagcagcggg aacaguucug cag                                           23
```

USE OF MICRO-RNA AS A BIOMARKER OF IMMUNOMODULATORY DRUG ACTIVITY

This application is a continuation of U.S. Ser. No. 12/340,472, filed Dec. 19, 2008, now U.S. Pat. No. 7,964,354, that claims priority to U.S. provisional application Ser. No. 61/008,824, filed Dec. 20, 2007, the entirety of which is incorporated herein by reference.

SEQUENCE LISTING

Filed with the present specification is a paper and computer readable form (CRF) copies of the Sequence Listing. The CRF entitled "10624-257-999-seqlist-final.txt" was created on Oct. 10, 2011 and is 1.51 kB in size, is identical to the paper copy of the Sequence Listing, and is incorporated herein by reference in its entirety.

1. FIELD OF THE INVENTION

This invention relates to the use of micro-RNAs to measure the presence, activity, or extent of a treatment by an immunomodulatory agent.

2. BACKGROUND

2.1 MicroRNAs

MicroRNAs (miRNAs) are small, single-stranded non-coding RNAs that can act in the cytoplasm of a cell to cause a decrease in the expression of their cognate target messenger RNAs or translation of the mRNA's protein product. Mature miRNAs are typically about 19-23 nucleotides in length. This ability of miRNAs to inhibit the production of their target proteins results in the regulation of many types of cellular activities, such as cell-fate determination, apoptosis, differentiation, and oncogenesis.

2.2 Immunomodulatory Compounds

The treatment of disease can be assisted by administration of many types of molecules that are capable of altering the immune system. For example, a number of studies have been conducted with the aim of providing compounds that can safely and effectively be used to treat diseases associated with abnormal production of TNF-α. See, e.g., Marriott, J. B., et al., *Expert Opin. Biol. Ther.* 1(4):1-8 (2001); G. W. Muller, et al., *Journal of Medicinal Chemistry*, 39(17): 3238-3240 (1996); and G. W. Muller, et al., *Bioorganic & Medicinal Chemistry Letters*, 8: 2669-2674 (1998). Some studies have focused on a group of compounds selected for their capacity to potently inhibit TNF-α production by LPS stimulated PBMC. (L. G. Corral, et al., *Ann. Rheum. Dis.*, 58 (suppl I): 1107-1113 (1999)). These immunomodulatory compounds, which include those referred to as IMiDs® brand Immunomodulatory products (Celgene Corporation), show not only potent inhibition of TNF-α but also marked inhibition of LPS induced monocyte IL1β, IL 12, and/or COX2 production. LPS induced IL6 is also partially inhibited by immunomodulatory compounds. These compounds are potent stimulators of LPS induced IL10. (Id.). Particular examples of immunomodulatory compounds include, but are not limited to, the substituted 2-(2,6-dioxopiperidin-3-yl) phthalimides and substituted 2-(2,6-dioxopiperidin-3-yl)-1-oxoisoindoles described and claimed in U.S. Pat. Nos. 6,281,230 and 6,316,471, both to G. W. Muller, et al., the entirety of both of which is incorporated herein by reference.

3. SUMMARY OF THE INVENTION

This invention relates to the use of miRNAs as biomarkers to ascertain the activity of immunomodulatory agents. For example, this invention relates to the finding that certain miRNAs, such as, but not limited to, miR-130a, miR-146b, miR-143, miR-145, miR-99b, miR-125a, miR-204, miR-424, and miR-503 are expressed at an altered level, e.g., up- or down-regulated, during administration of immunomodulatory compounds, and can thus be used to monitor patient progress during the treatment by immunomodulatory compounds.

In one embodiment provided herein, a method of assessing the activity (e.g., presence or extent of a treatment) of an immunomodulatory compound in a patient is provided. The method provided herein comprises obtaining a biological sample from the patient before and after the treatment, selecting at least one miRNA whose level of expression is increased or decreased in a cell treated with the immunomodulatory compound as compared to the level of expression without the treatment, measuring the level of the miRNA in the biological samples, and determining if the miRNA is present at an increased or decreased level in the biological sample obtained after the treatment as compared to the biological sample obtained before the treatment, where an increased or decreased level of the miRNA indicates the presence or activity of the treatment using an immunomodulatory compound. The miRNA may be, for example, miR-130a, miR-146b, miR-143, miR-145, miR-99b, miR-125a, miR-204, miR-424, or miR-503.

The treatment may be for a disease such as, but not limited to, a cancer, an immunological disorder, a viral infection, a fungal infection, a protozoal infection, and a bacterial infection. The treatment can be oral or parenteral administration of the immunomodulatory compound. The biological sample may be, for example, whole blood, partially purified blood, serum, a PBMC, or a tissue biopsy. The patient may be tested, for example, hourly, twice a day, daily, twice a week, weekly, twice a month, monthly, twice a year, yearly, or every other year. Examples of immunomodulatory compounds include, but are not limited to, N-{[2-(2,6-dioxo(3-piperidyl)-1,3-di-oxoisoindolin-4-yl]methyl}cyclopropyl-carboxamide, 3-[2-(2,6-dioxo-piperidin-3-yl)-1,3-dioxo-2,3-dihydro-1H-isoindol-4-ylmethyl]-1,1-dimethyl-urea, 1-oxo-2-(2,6-dioxopiperidin-3-yl)-4-aminoisoindoline, 1,3-dioxo-2-(2,6-dioxopiperidin-3-yl)-4-aminoisoindoline, 1-oxo-2-(2,6-dioxopiperidin-3-yl)-4-methylisoindoline, and N-[2-(2,6-Dioxo-piperidin-3-yl)-1,3-dioxo-2,3-dihydro-1H-isoindol-5-ylmethyl]-4-trifluoromethoxybenzamide.

In a specific embodiment, a method of assessing the activity of 1,3-dioxo-2-(2,6-dioxopiperidin-3-yl)-4-aminoisoindoline or 1-oxo-2-(2,6-dioxopiperidin-3-yl)-4-aminoisoindoline in a patient is provided. The method comprises obtaining a biological sample from the patient before and after the treatment, measuring the level of at least one miRNA (e.g., miR-130a, miR-146b, miR-143, miR-145, miR-99b, miR-125a, miR-204, miR-424, or miR-503) in the biological samples, and determining if the miRNA is present at an increased or decreased level in the biological sample obtained after the treatment compared to the miRNA level in the biological sample prior to the treatment, where an increased or decreased level of the miRNA indicates the activity of the compound, e.g., the presence or extent of the treatment. The treatment may be oral or parenteral administration of the immunomodulatory agent. The treatment may be for a disease such as, but not limited to, a cancer, an immunological disorder, a viral infection, a fungal infection, a protozoal infection, and a bacterial infection.

For example, provided herein is a method for assessing patient compliance with a drug treatment protocol. The method comprises selecting at least one miRNA biomarker that has an altered expression level in response to a drug treatment protocol, obtaining a biological sample from a patient, measuring the level of at least one miRNA biomarker in the sample, and determining if the level of the biomarker is altered in the patient sample compared to the level of the same biomarker in a control untreated sample, where an altered level of the biomarker indicates patient compliance with the drug treatment protocol. The altered expression level can be an increase in expression, or can be a decrease in expression.

In a yet further embodiment, a kit useful for assaying immunomodulatory activity is provided. The kit provided herein comprises a solid support and at least one oligonucleotide contacting the support, and a means for detecting the altered expression of the miRNA in the sample. The oligonucleotide corresponds to, for example, at least 5, 10, 15, 20, 25, 30 or more bases of at least one miRNA selected from miR-130a, miR-146b, miR-143, miR-145, miR-99b, miR-125a, miR-204, miR-424, and miR-503.

The assay may employ, for example, a dipstick, a membrane, a chip, a disk, a test strip, a filter, a microsphere, a slide, a multiwell plate, or an optical fiber. The solid support may have a component such as, but not limited to, a plastic, silicon, a metal, a resin, glass, a membrane, a particle, a precipitate, a gel, a polymer, a sheet, a sphere, a polysaccharide, a capillary, a film a plate, or a slide. The biological sample may be, for example, a cell lysate, a cell culture, a cell line, a tissue, an oral tissue, gastrointestinal tissue, an organ, an organelle, a biological fluid, a blood sample, a serum sample, a urine sample, or a skin sample.

In another embodiment, an oligonucleotide array for assessing immunomodulatory activity is provided. Such an array comprises a solid support and a plurality of oligonucleotides present on specific, addressable locations on the solid support. The oligonucleotides may correspond to, for example, at least a portion of sequences of an miRNA such as, but not limited to, miR-130a, miR-146b, miR-143, miR-145, miR-99b, miR-125a, miR-204, miR-424, or miR-503.

4. BRIEF DESCRIPTION OF FIGURES

5. DETAILED DESCRIPTION OF THE INVENTION

Figure 1A:
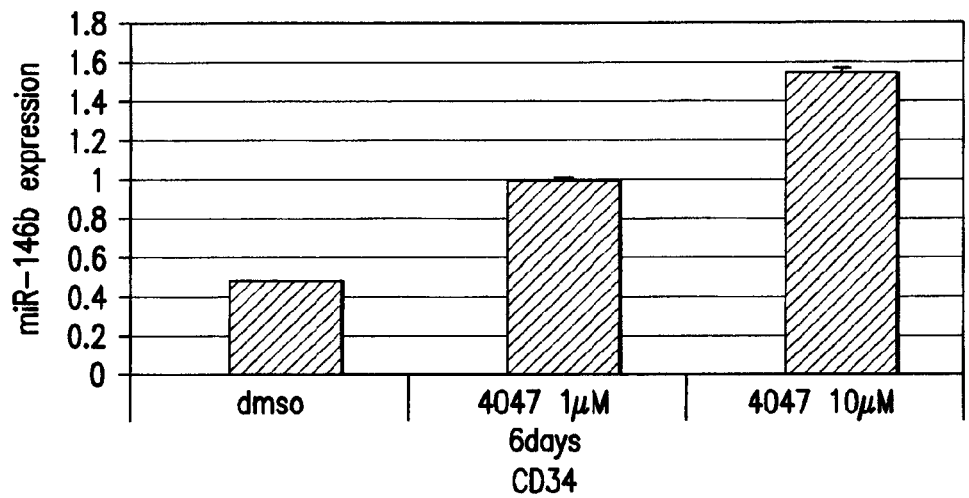
FIG. 1A is a bar graph illustrating miR-146b expression as measured by qRT-PCR in CD34 cells expanded and differentiated with Epo for 6 days in the presence of 0.1% DMSO or 1,3-dioxo-2-(2,6-dioxopiperidin-3-yl)-4-aminoisoindoline (1 or 10 µM).

This invention is based, in part, on the discovery that the presence and level of certain miRNAs in cell samples can be utilized as biomarkers to assess the activity (e.g., presence or extent of treatment) of an immunomodulatory compound. In particular, these miRNA biomarkers can be used to assess and track the activity of an immunomodulatory compound in a patient treated with such an immunomodulatory compound.

Without being limited by a particular theory, it was found that certain miRNAs, upon treatment by an immunomodulatory compound, exhibit an altered level of expression. Further without being limited by a particular theory, the level of expression of such miRNAs is correlated with the dose of the immunomodulatory compound and/or the length of the treatment. Thus, without being limited by a particular theory, by monitoring the level of expression of such miRNAs, it is possible to track or perform quality control on human research trials or to monitor the patient compliance to a drug regimen by providing a means to confirm that the patient is receiving specific drug treatments, i.e., in terms of the dose and time. The miRNA biomarkers can also be used to optimize dosing regimens. Thus, miRNA biomarkers can be used in connection with, for example, the management of patient treatment, clinical trials, and cell-based research.

5.1 Definitions

So that the invention is more fully understood, the following terms are more clearly defined:

An miRNA that is "upregulated" is generally increased upon a given treatment or condition. An miRNA that is "downregulated" generally refers to a decrease in the level of expression of the miRNA in response to a given treatment or condition. In some situations, the miRNA level can remain unchanged upon a given treatment or condition.

In general, an miRNA that is "differentially expressed" is one that is upregulated or downregulated between sample populations. In some embodiments, the difference in expression level can be measured qualitatively, such as the visualization of the presence or absence of a signal. In other embodiments, the level of miRNA can be determined quantitatively.

For example, an miRNA from a patient sample can be "upregulated" or "increased" when treated with an immunomodulatory compound, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control miRNA level (i.e., without the treatment by the immunomodulatory compound).

Alternatively, an miRNA can be "downregulated", or expressed at a lower level, or "reduced" in response to administration of an immunomodulatory compound. A downregulated miRNA can be, for example, present at a level of about 99%, 95%, 90%, 80%, 70%, 60%, 50%, 40%, 30%, 20%, 10%, 1% or less of the comparative control miRNA level (i.e., without the treatment by the immunomodulatory compound).

A "low" level of an miRNA in a sample can be a level that is less than the level of an miRNA in a pool from a non-patient population. A "low" level of a miRNA in a sample can also refer to a level that is decreased in comparison to the level of the miRNA reached upon treatment with an immunomodulatory compound. A "low" level of an miRNA can also refer to a level that is present in comparison to an individual that does not have a given disease. In certain cases, the low level of miRNA in a biological sample can be an indication that a specific disease is present.

A "high" level of an miRNA in a sample can be a level that is elevated in comparison to the level of an miRNA in a pool from a non-patient population. A "high" level of a miRNA in a sample can also refer to a level that is elevated in comparison to the level of the miRNA reached upon treatment with an immunomodulatory compound. A "high" level of an miRNA can also refer to a level that is present in comparison to an individual that does not have a given disease. In certain cases, a high level of miRNA in a biological sample can be an indication that a specific disease is present.

The term "immunomodulatory agent" or "immunomodulatory drug" or "immunomodulatory compound" generally refers to a molecule or compound, such as a small molecule or drug, an agent, a peptide, or a protein that can alter the immune system in some way.

The terms "immunomodulatory compounds" may encompass certain small organic molecules that inhibit LPS induced monocyte TNF-α, IL-1β, IL-12, IL-6, MIP-1α, MCP-1, GM-CSF, G-CSF, and COX-2 production. These compounds are useful for the treatment of many disorders, such as pain, inflammation, multiple myeloma, MDS (myelodysplastic syndromes), CLL (chronic lymphocytic leukemia), NHL (non-Hodgkin's lymphoma), solid tumors, and myelofibrosis. Examples of specific immunomodulatory compounds include, but are not limited to, those described herein elsewhere.

The terms "determining," "measuring," "evaluating," "assessing," and "assaying," as used herein, generally refer to any form of measurement, and include determining if an element is present or not. These terms include both quantitative and/or qualitative determinations. Assessing may be relative or absolute. The phrase "assessing the presence of" can include determining the amount of something present, as well as determining whether it is present or absent.

In addition, the phrase "assessing the activity of an immunomodulatory compound," as used herein, encompasses the assessment of the "presence" of the treatment by the immunomodulatory compound, e.g., whether the patient has been treated by or administered the immunomodulatory compound. The phrase also emcompasses the assessment of the "extent" of the treatment, e.g., doses and length of treatment determined in quantitative terms.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. An "oligonucleotide" is generally a molecule generally containing from about 2 to about 100 nucleotide subunits. As used herein in the context of a polynucleotide sequence, the term "bases" (or "base") is generally synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" generally refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" generally refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

"Sequence identity" or "identity" in the context of two nucleic acid sequences generally refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence. Another indication that nucleotide sequences are substantially identical is if two molecules hybridize to each other under stringent conditions.

As used herein, the term "bound" can be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

The terms "isolated" and "purified" generally refer to isolation of a substance (such as miRNA) such that the substance comprises a substantial portion of the sample in which it resides, i.e., greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more components of interest.

"Biological sample," as used herein, generally refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a serum sample, a urine sample, a skin sample, and the like. Preferred biological samples include but are not limited to whole blood, partially purified blood, PBMCs, tissue biopsies, and the like.

The term "analyte" as used herein, generally refers to a known or unknown component of a sample.

The term "capture agent," as used herein, generally refers to an agent that binds an miRNA through an interaction that is sufficient to permit the agent to bind and concentrate the miRNA from a homogeneous mixture of different miRNAs.

The term "probe" as used herein, generally refers to a capture agent that is directed to a specific target miRNA biomarker sequence. Accordingly, each probe of a probe set has a respective target miRNA biomarker. A probe/target miRNA duplex is a structure formed by hybridizing a probe to its target miRNA biomarker.

The term "nucleic acid or oligonucleotide probe" is generally defined as a nucleic acid capable of binding to a target nucleic acid of complementary sequence, such as the miRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target miRNA biomarker of interest.

The term "stringent assay conditions" generally refers to conditions that are compatible to produce binding pairs of nucleic acids, e.g., probes and target miRNAs, of sufficient complementarity to provide for the desired level of specificity in the assay while being generally incompatible to the formation of binding pairs between binding members of insufficient complementarity to provide for the desired specificity. The term stringent assay conditions generally refers to the combination of hybridization and wash conditions.

The term "array" and the equivalent term "microarray" generally refer to an ordered array of capture agents for binding to aqueous analytes such as miRNA. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. A typical array may contain one or more, including more than two, more than ten, more than one hundred, or more than one thousand features, in an area of less than about 100 $cm^2$, less than 20 $cm^2$, less than 10 $cm^2$, less than 5 $cm^2$, less than 1 $cm^2$, less than 1 $mm^2$, less than 100 $\mu m^2$, or even smaller. For example, features may have widths in the range from a 10 μm to 1.0 cm. In other embodiments each feature may have a width in the range of 1.0 μm to 1.0 mm, usually 5.0 μm to 500 μm, and more usually 10 μm to 200 p.m. Non-round features may have area ranges equivalent to that of circular features with the foregoing width (diameter) ranges. Inter-feature regions can be present which do not carry any nucleic acids. Such inter-feature areas are typically present where the arrays are formed by processes involving drop deposition of reagents but may not be present when, for example, photolithographic array fabrication processes are used.

A "label" or a "detectable moiety" in reference to a nucleic acid, generally refers to a composition that, when linked with a nucleic acid, renders the nucleic acid detectable, for example, by spectroscopic, photochemical, biochemical, immunochemical, or chemical means. Exemplary labels include but are not limited to radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

As used herein, and unless otherwise indicated, the term "optically pure" generally means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

5.2 miRNA Biomarkers

Mammalian genomes are thought to contain hundreds of miRNA genes. Mature endogenous miRNAs are typically short, noncoding single-stranded RNA molecules of about 19 to about 23 nucleotides long. Each of the miRNAs may be able to regulate a large number of proteins and pathways by decreasing the level of target transcripts or target proteins in a cell. As shown herein, the presence of certain of these miR-NAs in cell samples can be utilized as biomarkers for assessing the activity of an immunomodulatory compound. miR- NAs can be selected, for example, based on their upregulation or downregulation when a patient is treated with an immunomodulatory compound.

Therefore, in certain embodiments, the present invention is based, in part, on the inventor's discovery that certain miRNAs are differentially expressed in cell lines after treatment with certain immunomodulatory compounds. Such miRNAs can be identified and selected based on RNA expression profiling arrays, e.g., those similar to the procedures described in Example 6.3. Once identified and selected, the chosen miRNA biomarkers can be followed qualitatively or quantitatively, using any nucleic acid quantification methods known in the art such as, but not limited to, PCR-based methods.

The use of miRNAs, rather than other types of biomarkers such as messenger RNAs (mRNAs), has several benefits. Without being limited by a particular theory, the miRNA molecules are less prone to nuclease-mediated degradation than are typical mRNAs, making them easier to process and store without loss of signal. Additionally, without being limited by a particular theory, because there are fewer miRNAs than mRNAs, assay development, validation, and interpretation of the results are typically more straightforward.

In some embodiments, various cancer cell lines can be utilized to examine miRNA biomarker expression upon treatment with an immunomodulatory compound. Examples 6.1 through 6.9 provide illustrations of these methods using a CD34+ hematopoietic precursor cell model and a Namalwa lymphoma cell line model. To detect whether certain miRNAs are expressed after treatment with an immunomodulatory compound, RNA expression profiling can be initially performed to compare treated and untreated cells, as described in Example 6.3. miRNAs that are detected using this method can be examined further using any other desired detection methods, such as, but not limited to, PCR-based methods, such as the method described in Example 6.4.

In one embodiment, the miRNA biomarkers may be at least one of miR-130a (miRBase Accession No. MI0000448; SEQ ID NO: 1), miR-146b (miRBase Accession No. MI0003129; SEQ ID NO: 2), miR-143 (miRBase Accession No. MI0000459; SEQ ID NO: 3), and miR-145 (miRBase Accession No. MI0000461; SEQ ID NO: 4), miR-99b (miRBase Accession No. MIMAT0000689; SEQ ID NO: 5), miR-125a (miRBase Accession No. MIMAT0000443; SEQ ID NO: 6), miR-204 (miRBase Accession No. MIMAT0000265; SEQ ID NO: 7), miR-424 (miRBase Accession No. MIMAT0004749; SEQ ID NO: 8), and miR-503 (miRBase Accession No. MIMAT0002874; SEQ ID NO: 9), as listed in Table 1, below. As shown herein elsewhere, altered expression of these biomarkers in a sample can indicate the presence or extent of an immunomodulatory treatment regimen. However, other miRNA biomarkers can be identified and selected as desired by one of skill in the art, following the methods described herein.

TABLE 1

Selected Human miRNA Sequences

| Name | SEQ ID NO: | Mature miRNA Sequence | miRBase Accession No. |
|---|---|---|---|
| miR-130a | 1 | cagugcaauguuaaa agggcau | MI0000448 |
| miR-146b | 2 | ugagaacugaauucc auaggcu | MI0003129 |
| miR-143 | 3 | ugagaugaagcacug uagcuc | MI0000459 |
| miR-145 | 4 | guccaguuuucccag gaaucccu | MI0000461 |
| miR-99b | 5 | cacccguagaaccga ccuugcg | MIMAT0000689 |
| miR-125a | 6 | ucccugagacccuuu aaccuguga | MIMAT0000443 |
| miR-204 | 7 | uucccuuugucaucc uaugccu | MIMAT0000265 |
| miR-424 | 8 | caaaacgugaggcgc ugcuau | MIMAT0004749 |
| miR-503 | 9 | uagcagcgggaacag uucugcag | MIMAT0002874 | miRNA biomarkers can also be selected using cell-based assays. For example, tumor cell lines can be treated with immunomodulatory compounds, and miRNAs that are differentially expressed upon treatment can be determined.

In certain embodiments, the presence of miRNA biomarkers can be used to examine the activity of immunomodulatory agents on cells, cell cultures, tissues, or patients.

Nucleic acid probes corresponding to the miRNA biomarkers can be utilized in assays or arrays to detect miRNA levels in a sample. Methods of preparing and using nucleic acid probes and arrays are discussed herein and can be found in the art. For example, U.S. Patent Application Publication No. 20070092882, which is incorporated by reference herein in its entirety, provides methods of preparing and using probes and arrays to detect miRNA.

5.3 Immunomodulatory Compounds

Immunomodulatory compounds can be effective in treating many types of diseases, such as cancer, an immunological disorder, a viral infection, a fungal infection, a protozoal infection, a bacterial infection, or other diseases. In some embodiments, an immunomodulatory compound can be administered to a cell sample or to a patient, and its acticity (e.g., the presence or extent of the treatment) can be followed using miRNA biomarkers as described herein.

The immunomodulatory compounds provided herein encompass those known as IMiDs® brand Immunomodulatory products (Celgene Corporation). As used herein and unless otherwise indicated, the terms "immunomodulatory compounds" may encompass certain small organic molecules that inhibit LPS induced monocyte TNF-α, IL-1β, IL-12, IL-6, MIP-1α, MCP-1, GM-CSF, G-CSF, and COX-2 production.

Exemplary immunomodulatory compounds include, but are not limited to, N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (+3-(3,4-Dimethoxy-phenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-propionamide; (−)-{2-[1-(3-ethoxy-4-methoxyphenyl)-2-methylsulfonylethyl]-4-acetylaminoisoindoline- 1,3-dione}; (+)-{2-[1-(3-ethoxy-4-methoxyphenyl)-2-methylsulfonylethyl]-4-acetylaminoisoindoline-1,3-dione}; Difluoro-methoxy SelCIDs; 1-phthalimido-1-(3,4-diethoxyphenyl)ethane; 3-(3,4-dimethoxyphenyl)-3-(3,5-dimethoxyphenyl)acrylo nitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; Cyclopropyl-N-{2-[(1S)-1-(3-ethoxy-4-methoxyphenyl)-2-(methylsulfonyl)ethyl]-3-oxoisoindoline-4-yl}carboxamide; Substituted 2-(3-hydroxy-2,6-dioxopiperidin-5-yl) isoindoline; N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3S)-3-methyl-2,6-dioxo-piperidin-3-yl]-1,3-dioxo-2,3-dihydro-1H-isoindol-5-ylmethyl]-amide; (S)—N-((2-(3-methyl-2,6-dioxopiperidin-3-yl)-1,3-dioxoisoindolin-5-yl)methyl)-4-(trifluoromethyl)benzamide; 3-(2,5-dimethyl-4-oxo-4H-quinazolin-3-yl)-piperidine-2,6-dione, and the like.

The inflammatory cytokine TNF-α, which is produced by macrophages and monocytes during acute inflammation, causes a diverse range of signaling events within cells. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA.

Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. Pat. No. 7,091,353, and International Application No. PCT/US01/50401 (International Publication No. WO 02/059106). US patent publication no. 2006/0205787 describes 4-amino-2-(3-methyl-2,6-dioxopiperidin-3-yl)-isoindole-1,3-dione compositions. US patent publication no. 2007/0049618 describes isoindole-imide compounds. The entireties of each of the patents and patent applications identified herein are incorporated by reference. In one embodiment, immunomodulatory compounds do not include thalidomide.

Various immunomodulatory compounds disclosed herein contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. (See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972)).

Immunomodulatory compounds provided herein include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference.

These compounds have the structure I:

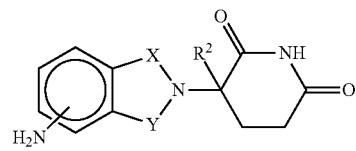

in which one of X and Y is C=O, the other of X and Y is C=O or CH$_2$, and R$^2$ is hydrogen or lower alkyl, in particular methyl. Specific immunomodulatory compounds include, but are not limited to:

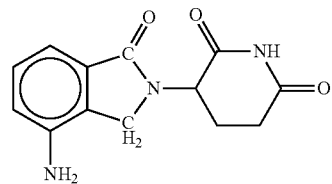

1-oxo-2-(2,6-dioxopiperidin-3-yl)-4-aminoisoindoline;

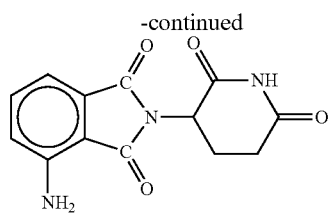

1,3-dioxo-2-(2,6-dioxopiperidin-3-yl)-4-aminoisindoline; and

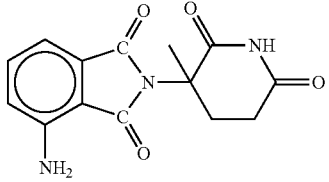

1,3-dioxo-2-(3-methyl-2,6-dioxopiperidin-3-yl)-4-aminoisoindole, and optically pure isomers thereof.

The compounds can be obtained via standard, synthetic methods (see e.g., U.S. Pat. No. 5,635,517, incorporated herein by reference). The compounds are also available from Celgene Corporation, Warren, N.J.

In another embodiment, specific immunomodulatory compounds encompass polymorphic forms of 1-oxo-2-(2,6-dioxopiperidin-3-yl)-4-aminoisoindoline; such as Form A, B, C, D, E, F, G and H, disclosed in U.S. publication no. US 2005/0096351 A1, which is incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

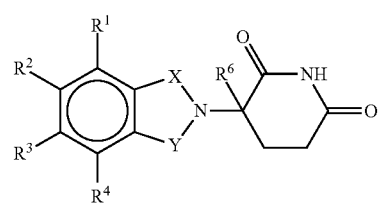

in which:
one of X and Y is C═O and the other of X and Y is C═O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;

$R^5$ is hydrogen or alkyl of 1 to 8 carbon atoms;

$R^6$ is hydrogen, alkyl of 1 to 8 carbon atoms, benzyl, or halo;

provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

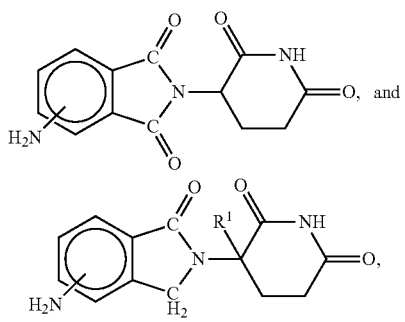

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds disclosed herein belong to a class of isoindole-imides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula II:

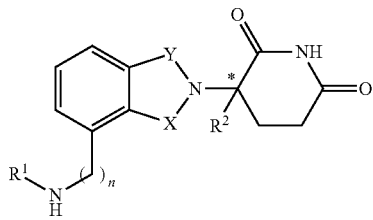

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl; each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O—R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)2$; $(C_0-C_8)$alkyl-NH—$C(O)O—R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

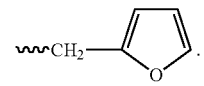

In another embodiment of the compounds of formula II, $R^1$ is

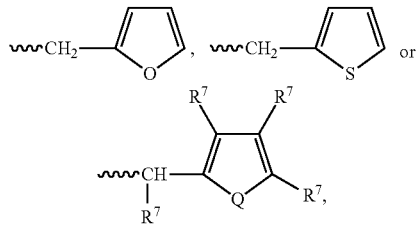

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with ($C_1$-$C_4$)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds disclosed herein belong to a class of isoindole-imides disclosed in U.S. Pat. No. 6,555,554, International Publication No. WO 98/54170, and U.S. Pat. No. 6,395,754, each of which is incorporated herein by reference. Representative compounds are of formula III:

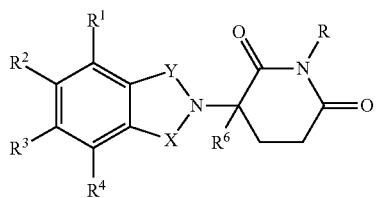

III and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—$N(R^8R^9)$;

$R^7$ is m-phenylene or p-phenylene or —(CnH2n)— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—;
$R^{10}$ is hydrogen, alkyl of to 8 carbon atoms, or phenyl; and
* represents a chiral-carbon center.

Other representative compounds are of formula:

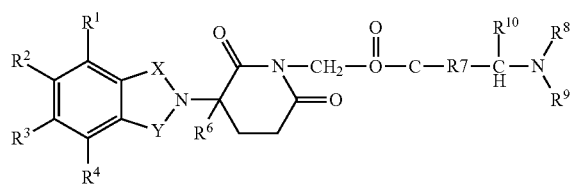

wherein:
one of X and Y is C=O and the other of X and Y is C=O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —(CnH2n)— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and
$R^{10}$ is hydrogen, alkyl of to 8 carbon atoms, or phenyl.

Other representative compounds are of formula:

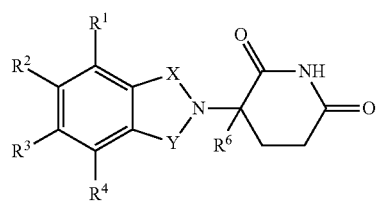

in which
one of X and Y is C=O and the other of X and Y is C=O or $CH_2$;
each of $R^1$, $R^2$, $R^3$, and $R^4$, independently of the others, is halo, alkyl of 1 to 4 carbon atoms, or alkoxy of 1 to 4 carbon atoms or (ii) one of R', $R^2$, $R^3$, and $R^4$ is nitro or protected amino and the remaining of R', $R^2$, $R^3$, and $R^4$ are hydrogen; and
$R^6$ is hydrogen, alkyl of 1 to 8 carbon atoms, benzo, chloro, or fluoro.

Other representative compounds are of formula:

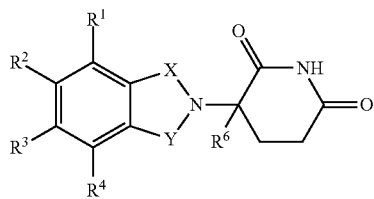

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R', R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and
R$^6$ is alkyl of 1 to 8 carbon atoms, benzo, chloro, or fluoro.

Specific examples of the compounds are of formula:

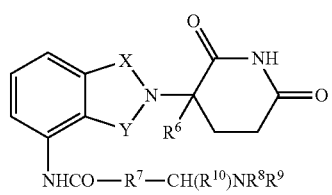

in which:
one of X and Y is C=O and the other of X and Y is C=O or CH$_2$;
R$^6$ is hydrogen, alkyl of 1 to 8 carbon atoms, benzyl, chloro, or fluoro;
R$^7$ is m-phenylene, p-phenylene or —(CnH2n)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and
R$^{10}$ is hydrogen, alkyl of 1 to 8 carbon atoms, or phenyl.

Other specific immunomodulatory compounds are 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

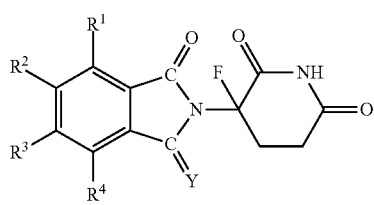

wherein:
Y is oxygen or H$_2$ and
each of R$^1$, R$^2$, R$^3$, and R$^4$, independently of the others, is hydrogen, halo, alkyl of 1 to 4 carbon atoms, alkoxy of 1 to 4 carbon atoms, or amino.

Other specific immunomodulatory compounds are the tetra substituted 2-(2,6-dioxopiperidin-3-yl)-1-oxoisoindolines described in U.S. Pat. No. 5,798,368, which is incorporated herein by reference. Representative compounds are of formula:

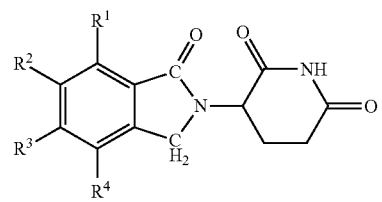

wherein each of R$^1$, R$^2$, R$^3$, and R$^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl) isoindolines disclosed in U.S. Pat. No. 6,403,613, which is incorporated herein by reference. Representative compounds are of formula:

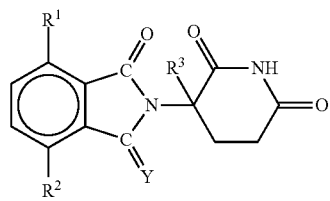

in which
Y is oxygen or H$_2$,
a first of R$^1$ and R$^2$ is halo, alkyl, alkoxy, alkylamino, dialkylamino, cyano, or carbamoyl, the second of R$^1$ and R$^2$, independently of the first, is hydrogen, halo, alkyl, alkoxy, alkylamino, dialkylamino, cyano, or carbamoyl, and
R$^3$ is hydrogen, alkyl, or benzyl.

Specific examples of the compounds are of formula:

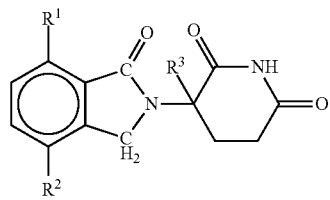

wherein
a first of R$^1$ and R$^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of R$^1$ and R$^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

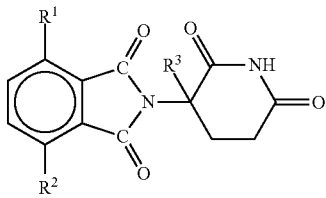

wherein:

a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl.

Other specific immunomodulatory compounds disclosed herein are 1-oxo and 1,3-dioxoisoindolines substituted in the 4- or 5-position of the indoline ring described in U.S. Pat. No. 6,380,239 and U.S. Pat. No. 7,244,759, both of which are incorporated herein by reference. Representative compounds are of formula:

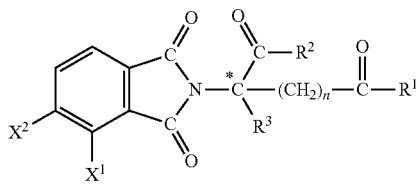

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

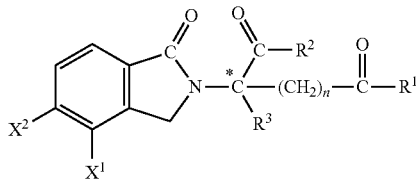

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

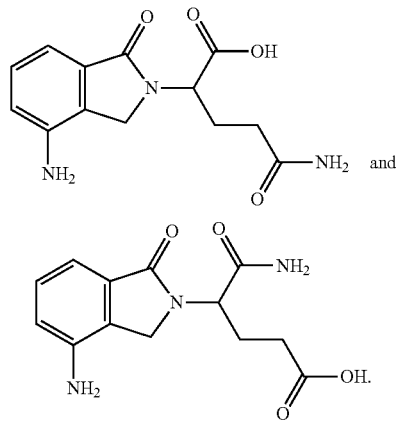

Other representative compounds are of formula:

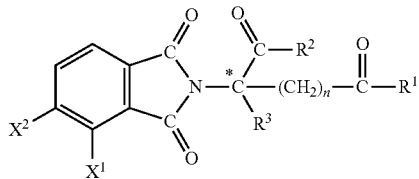

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

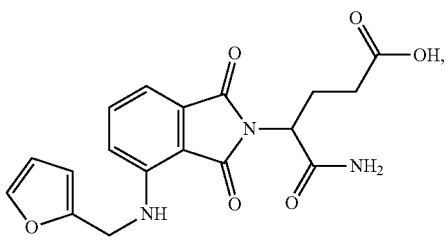

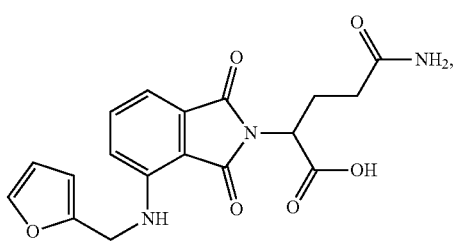

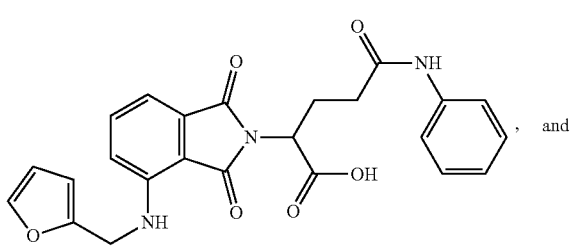, and

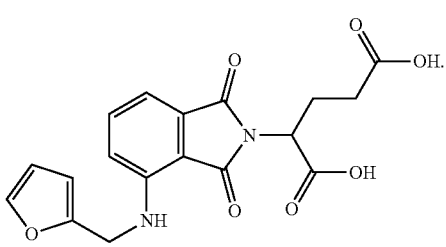

Other specific examples of the compounds are of formula:

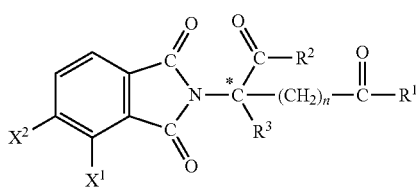

wherein:
one of $X^1$ and $X^2$ is nitro, or NH—Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —COR$^2$ and —(CH$_2$)$_n$COR$^1$ are different, the carbon atom designated C* constitutes a center of chirality.

Other representative compounds are of formula:

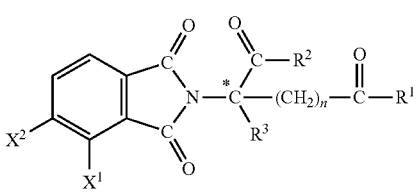

wherein:
one of $X^1$ and $X^2$ is alkyl of one to six carbons;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —COR$^2$ and —(CH$_2$)$_n$COR$^1$ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference.

Representative compounds are of formula:

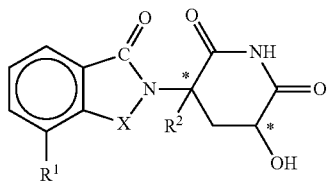

wherein:
the carbon atoms designated * constitute centers of chirality;

X is —C(O)— or —CH$_2$—;

$R^1$ is alkyl of 1 to 8 carbon atoms or —NHR$^3$;

$R^2$ is hydrogen, alkyl of 1 to 8 carbon atoms, or halogen; and $R^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —COR$^4$ in which $R^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

Still other specific immunomodulatory compounds disclosed herein belong to a class of 4'-O-substituted isoindoline derivatives disclosed in U.S. patent application Ser. No. 12/077,715, filed Mar. 19, 2008, which is incorporated herein by reference. Representative compounds are of the formula:

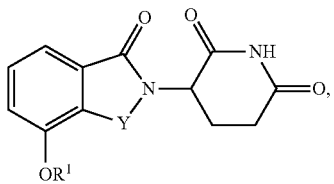

or a pharmaceutically acceptable salt, solvate, prodrug, clathrate, or stereoisomer thereof, wherein Y is C=O or CH$_2$, and R$^1$ is hydrogen, alkyl, alkenyl, alkynyl, aryl, aralkyl, cycloalkyl, cycloalkylalkyl, heterocyclyl, heterocyclylalkyl, heteroaryl, heteroarylalkyl, arylaminocarbonyl, alkylcarbonyl, alkylaminocarbonyl, dialkylaminocarbonyl, alkoxycarbonyl, cycloalkylcarbonyl, heteroarylcarbonyl or heterocyclylcarbonyl; where R$^1$ is optionally substituted with one or more, in certain embodiments, 1, 2, 3 or 4 substituents, one, two or three groups selected from alkoxy, halo, alkyl, carboxy, alkylaminocarbonyl, alkoxycarbonyl, nitro, amine, nitrile, haloalkyl, hydroxy, and alkylsulfonyl.

Still other specific immunomodulatory compounds disclosed herein belong to a class of isoindoline compounds disclosed in U.S. Provisional Patent Application Ser. No. 61/109,475, filed Oct. 29, 2008, which is incorporated herein by reference. Representative compounds are of the formula:

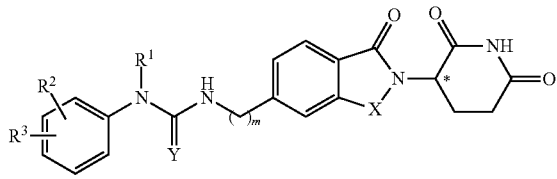

or a pharmaceutically acceptable salt, solvate, prodrug, or stereoisomer thereof, wherein:
X is C(=O) or CH$_2$;
Y is O, cyanamido (N=N), or amido (NH);
m is an integer of 0, 1, 2, or 3;
R$^1$ is hydrogen or C$_{1-6}$ alkyl;
R$^2$ is hydrogen, —NO$_2$, C$_{1-10}$ alkyl, C$_{0-6}$ alkyl-(5 to 10 membered heteroaryl), C$_{0-6}$ alkyl-(5 to 6 membered heterocyclyl), C$_{0-6}$ alkyl-OH, C$_{0-4}$ alkyl-NH$_2$, —NHCO—C$_{1-6}$ alkyl, —OR$^{21}$, or —(CH$_2$—Z)$_{0-2}$-(5 to 10 membered heteroaryl), where each heteroaryl and heterocyclyl is optionally substituted with one or more C$_{1-6}$ alkyl;
R$^3$ is hydrogen, halogen, —NO$_2$, C$_{0-6}$ alkyl-(5 to 10 membered heteroaryl), C$_{0-6}$ alkyl-(5 to 6 membered heterocyclyl), C$_{0-6}$ alkyl-OH, C$_{0-4}$ alkyl-NH$_2$, —NHCO—C$_{1-6}$ alkyl, —OR$^{21}$, or —(CH$_2$—Z)$_{0-2}$-(5 to 10 membered heteroaryl), where each heteroaryl and heterocyclyl is optionally substituted with one or more C$_{1-6}$ alkyl;
R$^{21}$ is C$_{6-10}$ aryl, 5 to 10 membered heteroaryl, 5 to 6 membered heterocyclyl, or —CO(CH$_2$)$_{0-2}$R$^{22}$, wherein the aryl, heteroaryl, and heterocyclyl are each optionally substituted with one or more C$_{1-6}$ alkyl;

R$^{22}$ is —NH$_2$ or 5 to 6 membered heterocyclyl; and
Z is CH$_2$, NH, or O;
with the proviso that when R$^1$ is hydrogen, then R$^2$ is not hydrogen or C$_{1-10}$ alkyl;
with the proviso that when Y is O, then R$^3$ is not halogen; and
with the proviso that when Y is O and R$^3$ is halogen, then R$^2$ is C$_{0-6}$ alkyl-(5-6 membered heterocyclyl).

In another embodiment, provided herein is a compound of the Formula:

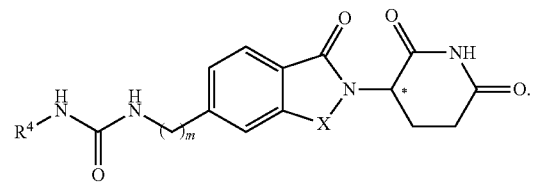

or a pharmaceutically acceptable salt, solvate, prodrug, or stereoisomer thereof, wherein:
X is C(=O) or CH$_2$;
m is an integer of 0, 1, 2, or 3;
R$^4$ is C$_{3-10}$ cycloalkyl, 5 to 10 membered heterocyclyl, 5 to 10 membered heteroaryl, or C$_{0-4}$ alkyl-NR$^{41}$R$^{42}$; wherein the cycloalkyl, heterocyclyl, and heteroaryl are each optionally substituted with one or more halogen, C$_{1-6}$ alkyl, —CO—NR$^{43}$R$^{44}$, —COOR$^{45}$, or C$_{0-4}$ alkyl-C$_{6-10}$ aryl, wherein the aryl itself may be optionally substituted with one or more halogen; and
R$^{41}$, R$^{42}$, R$^{43}$, R$^{44}$, and R$^{45}$ are each independently hydrogen or C$_{1-6}$ alkyl.

In yet another embodiment, provided herein is a compound of the Formula:

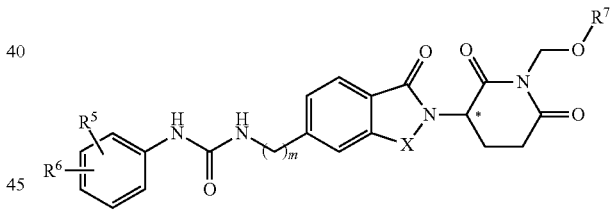

or a pharmaceutically acceptable salt, solvate, prodrug, or stereoisomer thereof, wherein:
X is C(=O) or CH$_2$;
m is an integer of 0, 1, 2, or 3;
R$^5$ and R$^6$ are each independently: hydrogen, halo, C$_{1-6}$ alkyl, oxo, —NO$_2$, C$_{1-6}$ alkoxy, —Z—C$_{1-6}$ alkyl, C$_{0-6}$ alkyl-(5 to 10 membered heteroaryl), C$_{0-6}$ alkyl-(5 to 6 membered heterocyclyl), C$_{0-6}$ alkyl-OH, C$_{0-4}$ alkyl-NH$_2$, —NHCO—C$_{1-6}$ alkyl, —OR$^{21}$, or —(CH$_2$—Y)$_{0-2}$-(5 to 10 membered heteroaryl),
wherein Z is S or SO$_2$;
wherein R$^{21}$ is as defined above;
wherein each heteroaryl and heterocyclyl above is optionally substituted with one or more C$_{1-6}$ alkyl; and
wherein the alkyl or alkoxy above may be optionally substituted with one or more: halogen; cyano; nitro; amino; C$_{1-6}$ alkylidenedioxy; C$_{1-6}$ alkoxy, itself optionally substituted with one or more halogens; or C$_{1-6}$ alkylthio, itself optionally substituted with one or more halogens;
R$^7$ is —COR$^{71}$ or —PO(OR$^{72}$)(OR$^{73}$);

R$^{71}$ is C$_{1-10}$ alkyl, C$_{6-10}$ aryl, or 5 to 6 membered heterocyclyl; wherein the alkyl, aryl, heterocyclyl may be optionally substituted with one or more amino, C$_{1-6}$ alkylamino, di(C$_{1-6}$ alkyl)amino, or —COOR$^{74}$; and R$^{72}$, R$^{73}$, and R$^{74}$ are ach independently hydrogen or C$_{1-10}$ alkyl.

In yet another embodiment, provided herein is a compound of the Formula:

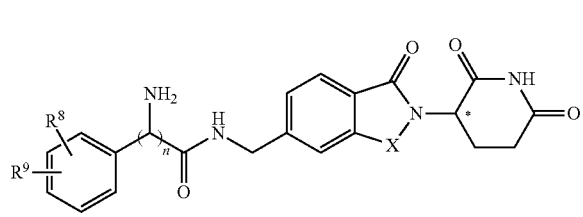

or a pharmaceutically acceptable salt, solvate, prodrug, or stereoisomer thereof, wherein:

X is C(=O) or CH$_2$;
n is an integer of 0 or 1;
R$^8$ is hydrogen or halo; and
R$^9$ is hydrogen, amino, or 5 to 10 membered heteroaryl or heterocyclyl;
with the proviso that when m is 1, R$^9$ is not hydrogen.

In yet another embodiment, provided herein is a compound of the Formula:

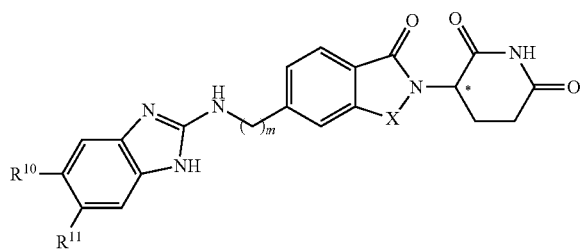

or a pharmaceutically acceptable salt, solvate, prodrug, or stereoisomer thereof, wherein:

X is C(=O) or CH$_2$;
m is an integer of 0, 1, 2, or 3;
R$^{10}$ and R$^{11}$ are each independently hydrogen, halo, C$_{1-6}$ alkyl, or C$_{6-10}$ aryloxy, wherein the alkyl and aryl are each optionally substituted with one or more halo.

In yet another embodiment, provided herein is a compound of the Formula:

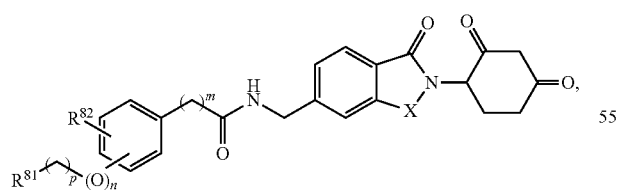

or a pharmaceutically acceptable salt, solvate, prodrug, or stereoisomer thereof, wherein:

X is CH$_2$ or C=O
m and n are each independently 0 or 1;
p is 0, 1, 2, or 3;
R$^{81}$ is 5 to 6 membered heterocyclyl, optionally substituted with C$_{1-6}$ alkyl; and
R$^{82}$ is hydrogen or halogen.

Still other specific immunomodulatory compounds disclosed herein belong to a class of 5′-substituted isoindoline derivatives disclosed in U.S. patent application Ser. Nos. 12/130,445 and 11/897,339, filed May 30, 2008 and Aug. 29, 2007, respectively, each of which is incorporated herein by reference. Representative compounds are of the formula:

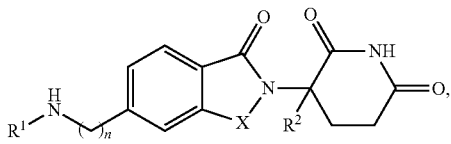

and pharmaceutically acceptable salts, solvates, stereoisomers, and prodrugs thereof, wherein:

n is 0 or 1;
X is CH$_2$, C=O, or C=S;
R$^1$ is:

a) —(CH$_2$)$_m$R$^3$ or —CO(CH$_2$)$_m$R$^3$, wherein
   m is 0, 1, 2, or 3; and
   R$^3$ is 5-10 membered aryl or heteroaryl, optionally substituted with one or more halogen;

b) —C=YR$^4$, wherein
   Y is O or S; and
   R$^4$ is:
      (C$_1$-C$_{10}$)alkyl; (C$_1$-C$_{10}$)alkoxy;
      (C$_0$-C$_{10}$)alkyl-(5 to 10 membered heteroaryl or heterocycle), said heteroaryl or heterocycle optionally substituted with one or more of (C$_1$-C$_6$)alkyl, halogen, oxo, (C$_1$-C$_6$)alkoxy, or —Z—(C$_1$-C$_6$)alkyl, wherein Z is S or SO$_2$, and wherein said (C$_1$-C$_6$) alkyl may be optionally substituted with one or more halogen;
      (C$_0$-C$_{10}$)alkyl-(5 to 10 membered aryl), said aryl optionally substituted with one or more of: halogen; (C$_1$-C$_6$)alkoxy, itself optionally substituted with one or more halogen; (C$_1$-C$_6$)alkyl, itself optionally substituted with one or more halogen; or —Z—(C$_1$-C$_6$)alkyl, wherein Z is S or SO$_2$, and wherein said (C$_1$-C$_6$)alkyl may be optionally substituted with one or more halogen; or
      (C$_1$-C$_6$)alkyl-CO—O—R$^{12}$, wherein R$^{12}$ is H or (C$_1$-C$_6$)alkyl; or c) —C=ZNHR$^6$, wherein
   Z is O or S; and
   R$^6$ is:
      (C$_1$-C$_{10}$)alkyl; (C$_1$-C$_{10}$)alkoxy;
      5 to 10 membered aryl or heteroaryl, optionally substituted with one or more of: halogen; cyano; (C$_1$-C$_6$)alkylenedioxy; (C$_1$-C$_6$)alkoxy, itself optionally substituted with one or more halogen; (C$_1$-C$_6$) alkyl, itself optionally substituted with one or more halogen; or (C$_1$-C$_6$)alkylthio, itself optionally substituted with one or more halogen; and R$^2$ is H or (C$_1$-C$_6$)alkyl.

Still other specific immunomodulatory compounds disclosed herein belong to a class of isoindole-imide compounds disclosed in U.S. Patent Application Publication No. US2007/0049618, which is incorporated herein by reference. Representative compounds are of the formula:

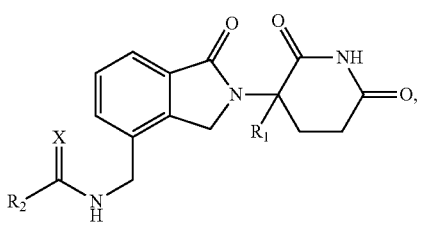

and pharmaceutically acceptable salts, solvates, stereoisomers, and prodrugs thereof,
wherein:
X is O or S;
R$_1$ is H or methyl;
R$_2$ is: (C$_2$-C$_6$)alkyl, excluding cycloalkyl; (C$_4$-C$_6$)cycloalkyl; (C$_1$-C$_4$)alkoxy;
(C$_1$-C$_6$)alkyl, substituted with (C$_1$-C$_4$)alkoxy;
(C$_0$-C$_1$)alkyl-phenyl, wherein the phenyl is optionally substituted with one or more of halogen, (C$_1$-C$_4$)alkoxy, (C$_1$-C$_4$)alkyl, or cyano;
(C$_0$-C$_1$)alkyl-(5 to 6 membered heteroaryl), wherein the heteroaryl is optionally substituted with one or more of (C$_1$-C$_4$)alkyl or halogen; or
(C$_0$-C$_3$)alkyl-NR$_3$R$_4$;
R$_3$ and R$_4$ are each independently:
H; (C$_1$-C$_6$)alkyl; (C$_3$-C$_6$)cycloalkyl;
(C$_0$-C$_1$)alkyl-(C$_6$-C$_{10}$)aryl, wherein the aryl is optionally substituted with one or more of (C$_1$-C$_4$)alkoxy, halogen, methyl, cyano, or —O—CH$_2$—O—;
(C$_0$-C$_1$)alkyl-(5 to 10 membered heteroaryl), wherein the heteroaryl is substituted with one or more of (C$_1$-C$_4$) alkoxy, halogen, or methyl; or C(O)R$_5$; and
R$_5$ is (C$_1$-C$_4$)alkoxy or (C$_1$-C$_2$)alkyl-O—(C$_1$-C$_2$)alkyl;
with the proviso that if one of R$_3$ and R$_4$ is H, then the other is not ethyl.

In one embodiment, X is O. In another embodiment, X is S. In another embodiment, R2 is phenyl, optionally substituted with one or more halogen.

In another embodiment, R2 is NHR4. In a specific embodiment, R4 is (C6-C10)aryl or 5 to 10 membered heteroaryl, both optionally substituted with one or more of (C1-C4) alkoxy, halogen, and methyl. In particular, the aryl or heteroaryl is phenyl, pyridyl, or naphthyl.

In another embodiment, this invention encompasses compounds of the formula:

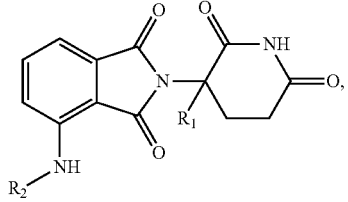

and pharmaceutically acceptable salts, solvates, stereoisomers, and prodrugs thereof, wherein:
R$_1$ is H or methyl; and
R$_2$ is: (C$_6$-C$_{10}$)aryl, optionally substituted with one or more of: (C$_1$-C$_8$)alkyl, optionally substituted with NH$_2$, NH(CH$_3$), or N(CH$_3$)$_2$; (C$_1$-C$_4$)alkoxy, optionally substituted with NH$_2$, NH(CH$_3$), N(CH$_3$)$_2$, or 3 to 6 membered heterocycloalkyl; (C$_3$-C$_6$)cycloalkyl; (C$_5$-C$_{10}$)aryloxy; hydroxy; NH$_2$; NH(CH$_3$); N(CH$_3$)$_2$; —CH$_2$—CH$_2$—CH$_2$—; halogen; or —O—CH$_2$—O—;
(C$_3$-C$_6$)alkyl, optionally substituted with one or more of (C$_1$-C$_4$)alkoxy;
(C$_1$-C$_2$)alkyl, optionally substituted with carboxyl;
(C$_1$-C$_6$)alkyl-(C$_3$-C$_6$)cycloalkyl; or
5 to 10 membered heterocycle;
with the proviso that if R$_2$ is pentyl, then R$_1$ is methyl.

In one embodiment, R$_2$ is phenyl, optionally substituted with one or more of (C$_1$-C$_4$)alkoxy or —O—CH$_2$—O—. In another embodiment, R$_2$ is phenyl substituted with one or more (C$_1$-C$_4$)alkoxy, substituted with N(CH$_3$)$_2$. In another embodiment, R$_2$ is (C$_3$-C$_6$)alkyl, optionally substituted with one or more of (C$_1$-C$_4$)alkoxy.

In another embodiment, this invention encompasses compounds of the formula:

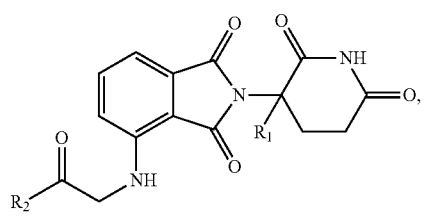

and pharmaceutically acceptable salts, solvates, stereoisomers, and prodrugs thereof,
wherein:
R$_1$ is H or methyl; and
R$_2$ is: amino, optionally substituted with one or more of (C$_1$-C$_6$)alkyl, (C$_3$-C$_6$)cycloalkyl, or phenyl; 3 to 6 membered heterocycloalkyl; or (C$_1$-C$_4$)alkoxy.

In one specific embodiment, R$_2$ is —NH(CH$_3$) or —N(CH$_3$)$_2$. In another embodiment, R$_2$ is (C$_3$-C$_6$)cycloalkyl.

In another embodiment, this invention encompasses compounds of the formula: or a pharmaceutically acceptable salt, solvate, stereoisomer, or prodrug thereof:

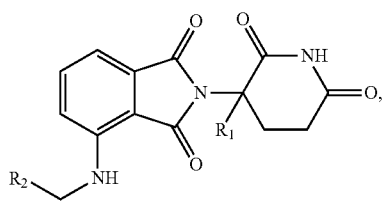

and pharmaceutically acceptable salts, solvates, stereoisomers, and prodrugs thereof, wherein R$_1$ is H or methyl; and R$_2$ is 5 to 6 membered heteroaryl;
with the proviso that if R$_2$ is furan or thiophene, then R$_1$ is methyl; and
with the proviso that if R$_2$ is pyridine, then the pyridine is not connected to the core at the 3 position.

In another embodiment, this invention encompasses compounds of the formula:

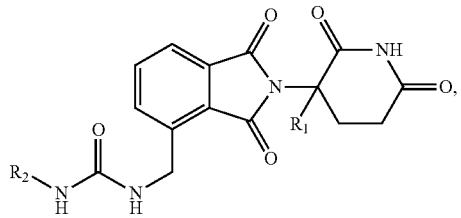

and pharmaceutically acceptable salts, solvates, stereoisomers, and prodrugs thereof:
wherein:
$R_1$ is H or methyl; and
$R_2$ is: H; methyl; ethyl;
  phenyl, substituted with one or more of ($C_1$-$C_6$)alkyl, halogen, ($C_1$-$C_4$)alkoxy, cyano, or —O—$CH_2$—O—;
  naphthyl, optionally substituted with one or more of ($C_1$-$C_6$)alkyl, halogen, ($C_1$-$C_4$)alkoxy, or cyano; or
  5 to 10 membered heteroaryl, optionally substituted with one or more of ($C_1$-$C_6$)alkyl, halogen, ($C_1$-$C_4$)alkoxy, or cyano;
with the proviso that if $R_2$ is ethyl, then $R_1$ is methyl; and
with the proviso that if $R_2$ is pyridine, then the pyridine is not connected to the core at the 3 position.

In another embodiment, this invention encompasses compounds of the formula:

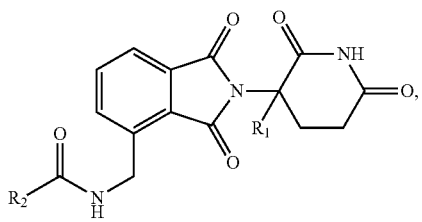

and pharmaceutically acceptable salts, solvates, stereoisomers, and prodrugs thereof, wherein:
$R_1$ is H or methyl; and
$R_2$ is: $N(CH_3)_2$;
  ($C_0$-$C_1$)alkyl-($C_6$-$C_{10}$)aryl, substituted with one or more of: methyl, itself optionally substituted with one or more halogen; ($C_1$-$C_4$)alkoxy, itself optionally substituted with one or more halogen; or halogen;
  ($C_0$-$C_1$)alkyl-(5 to 10 membered heteroaryl), optionally substituted with one or more of ($C_1$-$C_4$)alkyl, ($C_1$-$C_4$)alkoxy, or halogen; or
  (5 to 6 membered heteroaryl)-phenyl, wherein the heteroaryl and phenyl are each independently optionally substituted with one or more of ($C_1$-$C_4$)alkyl or ($C_1$-$C_4$)alkoxy;
with the proviso that $R_2$ is not unsubstituted pyridine, furan, or thiophene.

Still other specific immunomodulatory compounds disclosed herein belong to a class of N-methylaminomethyl isoindole compounds disclosed in U.S. Patent Application Publication No. US2008/0213615A1, which is incorporated herein by reference.

Representative compounds are of the formula:

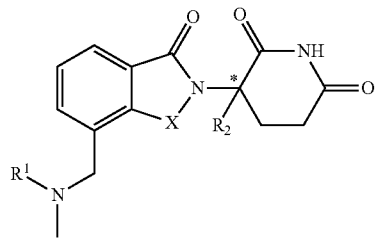

and pharmaceutically acceptable salts, solvates, stereoisomers, and prodrugs thereof, wherein:
\* denotes chiral center;
X is $CH_2$ or C=O;
$R^1$ is H, ($C_1$-$C_8$)alkyl, ($C_3$-$C_7$)cycloalkyl, ($C_2$-$C_8$)alkenyl, ($C_2$-$C_8$)alkynyl, benzyl, aryl, ($C_0$-$C_4$)alkyl-($C_1$-$C_6$)heterocycloalkyl, ($C_0$-$C_4$)alkyl-($C_2$-$C_9$)heteroaryl, C(O)$R^3$, C(S)$R^3$, C(O)O$R^4$, ($C_1$-$C_8$)alkyl-N($R^6$)$_2$, ($C_1$-$C_{18}$)alkyl-O$R^5$, ($C_1$-$C_8$)alkyl-C(O)O$R^5$, C(O)NH$R^3$, C(S)NH$R^3$, C(O)N$R^3R^{3'}$, C(S)N$R^3R^{3'}$ or ($C_1$-$C_8$)alkyl-O(CO)$R^5$;
$R^2$ is H, $CH_3$, or ($C_2$-$C_8$)alkyl;
$R^3$ and $R^{3'}$ are independently
  ($C_1$-$C_8$)alkyl;
  ($C_3$-$C_7$)cycloalkyl;
  ($C_2$-$C_8$)alkenyl;
  ($C_2$-$C_8$)alkynyl;
  benzyl;
  ($C_0$-$C_4$)alkyl-($C_5$-$C_{10}$)aryl, optionally substituted with one or more of:
    ($C_1$-$C_6$)alkyl, said alkyl itself optionally substituted with one or more halogen,
    ($C_1$-$C_6$)alkoxy, said alkoxy itself optionally substituted with one or more halogen,
    $SCY_3$, wherein Y is hydrogen or halogen,
    $NZ_2$, wherein Z is hydrogen or ($C_1$-$C_6$)alkyl
    ($C_1$-$C_6$)alkylenedioxy, or
    halogen;
  ($C_0$-$C_4$)alkyl-($C_1$-$C_6$)heterocycloalkyl;
  ($C_0$-$C_4$)alkyl-($C_2$-$C_9$)heteroaryl;
  ($C_0$-$C_8$)alkyl-N($R^6$)$_2$;
  ($C_1$-$C_8$)alkyl-O$R^5$;
  ($C_1$-$C_8$)alkyl-C(O)O$R^5$;
  ($C_1$-$C_8$)alkyl-O(CO)$R^5$; or
  C(O)O$R^5$;
$R^4$ is ($C_1$-$C_8$)alkyl, ($C_2$-$C_8$)alkenyl, ($C_2$-$C_8$)alkynyl, ($C_1$-$C_4$)alkyl-O$R^5$, benzyl, aryl, ($C_0$-$C_4$)alkyl-($C_1$-$C_6$)heterocycloalkyl, or ($C_0$-$C_4$)alkyl-($C_2$-$C_9$)heteroaryl;
$R^5$ is ($C_1$-$C_8$)alkyl, ($C_2$-$C_8$)alkenyl, ($C_2$-$C_8$)alkynyl, benzyl, ($C_5$-$C_{10}$)aryl, or ($C_2$-$C_9$)heteroaryl;
each occurrence of $R^6$ is independently H, ($C_1$-$C_8$)alkyl, ($C_2$-$C_8$)alkenyl, ($C_2$-$C_8$)alkynyl, benzyl, ($C_5$-$C_{10}$)aryl, ($C_2$-$C_9$)heteroaryl, or ($C_0$-$C_8$)alkyl-C(O)O—$R^5$, or
two $R^6$ groups can join to form a heterocycloalkyl group.

Still other specific immunomodulatory compounds disclosed herein belong to a class of 5-substituted quinazolinone derivatives disclosed in U.S. Patent Application Publication No. US2008/016328A1, which is incorporated herein by reference. Representative compounds are of the formula:

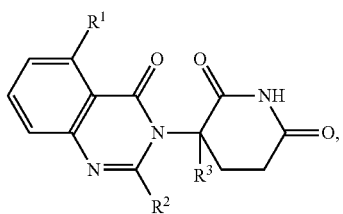

and pharmaceutically acceptable salts, solvates, and stereoisomers thereof, wherein:

$R^1$ is: hydrogen; halo; —$(CH_2)_n OH$; $(C_1-C_6)$alkyl, optionally substituted with one or more halo; $(C_1-C_6)$alkoxy, optionally substituted with one or more halo; or
—$(CH_2)_n NHR^a$, wherein $R^a$ is:
hydrogen;
$(C_1-C_6)$alkyl, optionally substituted with one or more halo;
—$(CH_2)_n$-(6 to 10 membered aryl);
—$C(O)$—$(CH_2)_n$-(6 to 10 membered aryl) or —$C(O)$—$(CH_2)_n$(6 to 10 membered heteroaryl), wherein the aryl or heteroaryl is optionally substituted with one or more of: halo; —$SCF_3$; $(C_1-C_6)$alkyl, itself optionally substituted with one or more halo; or $(C_1-C_6)$alkoxy, itself optionally substituted with one or more halo;
—$C(O)$—$(C_1-C_8)$alkyl, wherein the alkyl is optionally substituted with one or more halo;
—$C(O)$—$(CH_2)_n$—$(C_3-C_{10}$-cycloalkyl);
—$C(O)$—$(CH_2)_n$—$NR^b R^c$, wherein $R^b$ and $R^c$ are each independently:
hydrogen;
$(C_1-C_6)$alkyl, optionally substituted with one or more halo;
$(C_1-C_6)$alkoxy, optionally substituted with one or more halo; or
6 to 10 membered aryl, optionally substituted with one or more of: halo; $(C_1-C_6)$alkyl, itself optionally substituted with one or more halo; or $(C_1-C_6)$alkoxy, itself optionally substituted with one or more halo;
—$C(O)$—$(CH_2)_n$—$O$—$(C_1-C_6)$alkyl; or
—$C(O)$—$(CH_2)_n$—$O$—$(CH_2)_n$-(6 to 10 membered aryl);

$R^2$ is: hydrogen; —$(CH_2)_n OH$; phenyl; —$O$—$(C_1-C_6)$alkyl; or $(C_1-C_6)$alkyl, optionally substituted with one or more halo;

$R^3$ is: hydrogen; or $(C_1-C_6)$alkyl, optionally substituted with one or more halo; and n is 0, 1, or 2.

Still other specific immunomodulatory compounds disclosed herein belong to a class of thioxoisoindoline compounds disclosed in U.S. Provisional Patent Application No. 61/127,422, which is incorporated herein by reference. Representative compounds are of the formula:

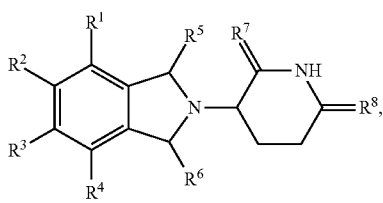

and pharmaceutically acceptable salts, solvates, and stereoisomers thereof, wherein one of $R^1$-$R^4$ is $NH_2$ or $NO_2$, and the others of $R^1$-$R^4$ are each hydrogen; $R^5$ and $R^6$ are each independently thioxo or hydrogen, provided that at least one of $R^5$ or $R^6$ is thioxo; and $R^7$ and $R^8$ are each independently thioxo or oxo.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. US20060188475, US20060205787, and US20070049618, each of which is incorporated by reference herein in its entirety.

The compounds may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.4 Methods of Administration of Immunomodulatory Compounds

In some embodiments, the one or more immunomodulatory compounds or a pharmaceutically acceptable salt, solvate, stereoisomer, tautomer, or prodrug thereof, is administered to a subject (e.g., a human), and the presence or extent of the treatment is monitored by following selected miRNA biomarkers.

Any route of administration may be used. For example, an immunomodulatory compound can be administered by oral, parenteral, intravenous, transdermal, intramuscular, rectal, sublingual, mucosal, nasal, or other means. In addition, an immunomodulatory compounds can be administered in a form of pharmaceutical composition and/or unit dosage form. Suitable dosage forms include, but are not limited to, capsules, tablets (including rapid dissolving and delayed release tablets), powder, syrups, oral suspensions and solutions for parenteral administration. Suitable administration methods for the immunomodulatory compounds, as well as suitable dosage forms and pharmaceutical compositions, can be found in U.S. Patent Application Publication Nos. US20060188475, US20060205787, and US20070049618, each of which is incorporated by reference herein in its entirety.

The specific amount of the agent will depend on the specific agent used, the type of disease or disorder being treated or managed, and the amount(s) of an immunomodulatory compound provided herein and any optional additional agents concurrently administered to the patient. Typical dosage forms comprise an immunomodulatory compound or a pharmaceutically acceptable salt, solvate, stereoisomer, or prodrug thereof in an amount of from about 0.001 to about 150 mg. In particular, dosage forms comprise an immunomodulatory compound or a pharmaceutically acceptable salt, solvate, stereoisomer, or prodrug thereof in an amount of about 0.001, 0.01, 0.1, 1, 2, 5, 7.5, 10, 12.5, 15, 17.5, 20, 25, 50, 100, 150 or 200 mg. In a particular embodiment, a dosage form comprises 4-(amino)-2-(2,6-dioxo(3-piperidyl))-isoindoline-1,3-dione in an amount of about 0.001, 0.01, 0.1, 1, 2, 5, 10, 25 or 50 mg.

Pharmaceutical compositions provided herein can also contain one of more pharmaceutically acceptable excipients. See, e.g., Rowe et al., Handbook of Pharmaceutical Excipients, 4$^{th}$ Ed. (2003), the entirety of which is incorporated herein by reference.

In some embodiments, an immunomodulatory compound is administered to a subject about 3 months, 30 days, 20 days, 15 days, 12 days, 10 days, 7 days, 5 days, 3 days, 1 day, 12 hours, or 5 hours prior to testing for miRNA biomarker levels. In other embodiments, an immunomodulatory compound is administered from about 3 months to about 30 days, 30 days to about 5 hours, from about 20 days to about 5 hours, from about 15 days to about 12 hours, from about 12 days to about 5 hours, from about 10 days to about 12 hours, from about 7 days to about 12 hours, from about 5 days to about 12 hours, from about 5 days to about 1 day, from about 3 days to about 12 hours, or from about 3 days to about 1 day prior to testing for miRNA biomarker levels.

In some embodiments, this invention encompasses miRNA biomarker-based monitoring upon administration of racemic mixture, optically pure (R)-isomer, or optically pure (S)-isomer of 4-(amino)-2-(2,6-dioxo(3-piperidyl))-isoindoline-1,3-dione. In one specific embodiment, the racemic 4-(amino)-2-(2,6-dioxo(3-piperidyl))-isoindoline-1,3-dione is administered at an amount of 1, 2, 5, 10, or 25 mg per day. As (S)-isomer of 4-(amino)-2-(2,6-dioxo(3-piperidyl))-isoindoline-1,3-dione is reported to have a higher potency than the racemic mixture, a lower dose can be given when (S)-isomer is used. For example, (S)-4-(amino)-2-(2,6-dioxo (3-piperidyl))-isoindoline-1,3-dione can be administered at an amount of 0.01, 0.1, 1. 2.5, 5, or 10 mg per day. The (R)-isomer of 4-(amino)-2-(2,6-dioxo(3-piperidyl))-isoindoline-1,3-dione can be administered at an amount comparable to the racemic mixture.

In a specific embodiment, a dosage form comprises 3-(4-amino-1-oxo-1,3-dihydro-isoindol-2-yl)-piperidine-2,6-dione in an amount of about 0.001, 0.01, 0.1, 1, 5, 10, 25 or 50 mg. Typical dosage forms comprise the second active ingredient in an amount of 1 μg to about 1000 mg, from about 0.01 to about 500 mg, from about 0.1 to about 350 mg, or from about 1 to about 200 mg. This invention also encompasses the use of racemic mixture, (S)-isomer, and (R)-isomer of 3-(4-amino-1-oxo-1,3-dihydro-isoindol-2-yl)-piperidine-2,6-dione. Typically, racemic 3-(4-amino-1-oxo-1,3-dihydro-isoindol-2-yl)-piperidine-2,6-dione can be administered at an amount of 1, 5, 10, 15, 25, or 50 mg per day. Optical isomers also can be administered at an amount comparable to racemic mixture. Doses can be adjusted depending on the type of disease or disorder being treated, prevented or managed, and the amount of an immunomodulatory compound and any optional additional agents concurrently administered to the patient, which are all within the skill of the art.

5.5 Methods of Detecting miRNA Levels in a Sample

The presence of miRNA biomarkers can be used to examine the activity of immunomodulatory agents on cells, tissues, or patients. In one embodiment, the miRNA biomarkers are chosen from miR-130a, miR-146b, miR-143, miR-145, miR-99b, miR-125a, miR-204, miR-424, and miR-503. However, other miRNA biomarkers can be selected for use as described herein. Nucleic acid assays or arrays can be used to assess the presence and/or levels of one or more miRNAs a sample. Any suitable method of detecting or assaying for selected miRNAs can be used. In some embodiments, one or two selected miRNAs are assessed. In other embodiments, more than one or two miRNAs are assessed.

Thus, in some embodiments, an oligonucleotide array for testing for immunomodulatory activity in a biological sample can be prepared or purchased. An array typically contains a solid support and at least one oligonucleotide contacting the support, where the oligonucleotide corresponds to at least a portion of an miRNA that has altered expression during an immunomodulatory treatment in a patient. In some embodiments, the portion of an miRNA comprises at least 5, 10, 15, 20, 25, 30 or more bases.

Assays can include a means for detecting the altered expression of the miRNA in the sample. Exemplary biological samples include, but are not limited to, a cell lysate, a cell culture, a cell line, a tissue, an oral tissue, gastrointestinal tissue, an organ, an organelle, a biological fluid, a blood sample, a serum sample, a urine sample, a skin sample, and the like.

The assay method can be varied depending on the type of miRNA information desired. For example, an initial differential expression assay to determine which miRNAs are upregulated can be performed using an oligonucleotide array. When an miRNA that is differentially expressed is identified and selected, corresponding probes can be made to test samples for the presence of the selected miRNA biomarker, using any methods known in the art, such as, but not limited to, Northern blots and PCR-based methods (e.g., qRT-PCR). Methods such as qRT-PCR can also accurately quantitate the amount of the miRNA in a sample.

Any suitable assay platform can be used to determine the presence of the miRNA in a sample. For example, an assay may be in the form of a dipstick, a membrane, a chip, a disk, a test strip, a filter, a microsphere, a slide, a multiwell plate, or an optical fiber. An assay system may have a solid support on which an oligonucleotide corresponding to the miRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an miRNA. Exemplary preparation of various types of miRNA assays is described herein elsewhere.

The comparative sample populations can be obtained from various sources. In some embodiments, a first population of miRNAs and a second population of miRNAs are produced from two different miRNA-containing samples. The two different samples can be obtained from several sources, depending on the type of assessment desired. For example, the two samples can be from a first and second patient (or patient population), one with a disease and one without a disease. Alternatively, the two samples can be from a first and second patient (or patient population) both having a disease, in which the first sample has been treated with an immunomodulatory compound, while the other has received no treatment. The two samples can be a first and second tissue or blood sampling of an individual, one prior to and one after treatment. The two samples can be a first and second cell (or cell culture), wherein the first cell is a positive or negative control, and the second cell is contacted with an immunomodulatory drug. Multiple samples can be compared, such as between patients, or chronological samplings during clinical trials.

The sample can be labeled, if desired, to make a population of labeled miRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2', 4',7',4,7-hexachlorofluorescein (HEX), 6 carboxy 4',5' dichloro 2',7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

5.6 Differential Expression Arrays

As described herein, several specific miRNAs including, but not limited to, miR-130a, miR-146b, miR-143, miR-145, miR-99b, miR-125a, miR-204, miR-424, and miR-503 have been found to be differentially expressed upon administration of immunomodulatory compounds and can thus be utilized as biomarkers. Furthermore, by use of the methods described herein, other miRNAs can also be identified and selected to be used as biomarkers. For example, a differential expression array, described herein below, can be used to identify and select new miRNA biomarker sequences.

In some embodiments, an array can be used to assess the expression of multiple miRNAs in a sample. In general, the method comprises the following steps: a) contacting the sample with an array comprising a probe set under conditions sufficient for specific binding to occur; and b) examining the array to detect the presence of any detectable label, thereby evaluating the amount of the respective target miRNAs in the sample. Methods of preparing assays or arrays for assaying miRNAs can be found, for example, in U.S. Patent Application Publication No. 20070092882, which is incorporated by reference herein in its entirety.

For example, the method may involve obtaining a biological sample, treating the sample with an immunomodulatory compound, obtaining an miRNA expression profile of the sample using an expression array, and then selecting an miRNA which is differentially expressed as compared to cells that have not received the immunomodulatory treatment. Using this method, a biomarker for immunomodulatory activity can be obtained.

In general, a differentially expressed miRNA is one that is upregulated (increased) or downregulated (decreased) between sample populations. This expression can be measured by any suitable method, including quantitative and qualitative methods.

Nucleic acid arrays can be used to detect differential expression of miRNAs in biological samples. Analytic methods employing polynucleotide arrays have been used for investigating small RNAs, e.g. miRNAs have become a subject of investigation with microarray analysis. (See, e.g., Liu et al., *Proc. Nat'l Acad. Sci. USA*, 101: 9740-9744 (2004); Thomson et al., *Nature Methods*, 1:47-53 (2004); and Babak et al., *RNA*, 10:1813-1819 (2004)). Polynucleotide arrays (such as DNA or RNA arrays) typically include regions of usually different sequence polynucleotides ("capture agents") arranged in a predetermined configuration on a support. The arrays are "addressable" in that these regions (sometimes referenced as "array features") have different predetermined locations ("addresses") on the support of array. The polynucleotide arrays typically are fabricated on planar supports either by depositing previously obtained polynucleotides onto the support in a site specific fashion or by site specific in situ synthesis of the polynucleotides upon the support. After depositing the polynucleotide capture agents onto the support, the support is typically processed (e.g., washed and blocked for example) and stored prior to use.

A nucleic acid array may be contacted with a sample or labeled sample containing miRNA analytes under conditions that promote specific binding of the miRNA in the sample to one or more of the capture agents present on the array. Thus, without being limited by a particular theory, the arrays, when exposed to a sample, can undergo a binding reaction with the sample to exhibit an observed binding pattern. This binding pattern can be detected upon interrogating the array. For example, the target miRNAs in the sample can be labeled with a suitable label (such as a fluorescent compound), and the label then can be accurately observed (such as by observing the fluorescence pattern) on the array after exposure of the array to the sample. The observed binding pattern can be indicative of the presence and/or concentration of one or more miRNA components of the sample.

In some embodiments, an oligonucleotide array for assessing immunomodulatory activity can be prepared or purchased (available from, e.g., Ambion or Exiqon). The array may contain a solid support and a plurality of oligonucleotides contacting the support. The oligonucleotides may be present in specific, addressable locations on the solid support; each corresponding to at least a portion of miRNA sequences that are differentially expressed upon treatment of an immunomodulatory compound in a cell or a patient. In some embodiments, the miRNA sequences comprise at least one miRNA selected from the group consisting of miR-130a, miR-146b, miR-143, miR-145, miR-99b, miR-125a, miR-204, miR-424, and miR-503.

Arrays to detect miRNA expression can be fabricated by depositing (e.g., by contact- or jet-based methods or photolithography) either precursor units (such as nucleotide or amino acid monomers) or pre-synthesized capture agent. An array is "addressable" when it has multiple regions of different moieties (e.g., different capture agents) such that a region (i.e., a "feature" or "spot" of the array) at a particular predetermined location (i.e., an "address") on the array will detect a particular miRNA target. An "array layout" refers to one or more characteristics of the features, such as feature positioning on the support, one or more feature dimensions, and an indication of a moiety at a given location.

In some embodiments, an array to detect miRNA expression has at least two, three, four, or five different subject probes. However, in certain embodiments, a subject array may include a probe set having at least 10, at least 20, at least 50, at least 100, at least 200, at least 500, or at least 1,000 or more probes that can detect a corresponding number of miRNAs. In some embodiments, the subject arrays may include probes for detecting at least a portion or all of the identified miRNAs of an organism, or may include orthoogous probes from multiple organisms.

When an array is used to assess miRNAs, a typical method can contain the steps of 1) obtaining the array containing surface-bound subject probes; 2) hybridization of a population of miRNAs to the surface-bound probes under conditions sufficient to provide for specific binding (3) post-hybridization washes to remove nucleic acids not bound in the hybridization; and (4) detection of the hybridized miRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on an array surface between complementary binding members, i.e., between surface-bound subject probes and complementary miRNAs in a sample. In certain embodiments, stringent hybridization conditions may be employed.

Hybridization is typically performed under stringent hybridization conditions. Standard hybridization techniques (e.g. under conditions sufficient to provide for specific binding of target miRNAs in the sample to the probes on the array) are used to hybridize a sample to a nucleic acid array. Suitable methods are described in Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

In general, a "stringent hybridization" and "stringent hybridization wash conditions" in the context of nucleic acid hybridization are typically sequence dependent, and are different under different experimental conditions. Stringent hybridization conditions that can be used to identify nucleic acids can include, e.g., hybridization in a buffer comprising 50% formamide, 5×SSC, and 1% SDS at 42° C., or hybridization in a buffer comprising 5×SSC and 1% SDS at 65° C., both with a wash of 0.1×SSC and 0.1% SDS at 37° C. Exemplary stringent hybridization conditions can also include a hybridization in a buffer of 40% formamide, 1M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Hybridization buffers suitable for use in the methods described herein are well known in the art and may contain salt, buffer, detergent, chelating agents and other components at pre-determined concentrations. In one embodiment, hybridization is done over a period of about 12 to about 24 hours.

The stringency of the wash conditions can affect the degree to which miRNA sequences are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/ 0.1% SDS at 42° C. In instances wherein the nucleic acid molecules are deoxyoligonucleotides (i.e., oligonucleotides), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See, e.g., Ausubel, et al., Short Protocols in Molecular Biology, 3rd ed., Wiley & Sons (1995); Sambrook et al., Molecular Cloning: A Laboratory Manual, Third Edition, Cold Spring Harbor, N.Y. (2001); or Tijssen, Hybridization with Nucleic Acid Probes, Parts I and II (Elsevier, Amsterdam 1993), for detailed descriptions of equivalent hybridization and wash conditions and for reagents and buffers, e.g., SSC buffers and equivalent reagents and conditions. Those of ordinary skill will readily recognize that alternative but comparable hybridization and wash conditions can be utilized to provide conditions of similar stringency.

As an illustration, in one embodiment, the miRNA expression profiling experiments may be conducted according to protocols described in Ambion mirVana™ miRNA Bioarrays instruction manual. Briefly, the procedures are as follows: previously labeled and purified miRNA is mixed with 3× miRNA Hybridization Buffer, heated to 95° C. for 2 minutes, and hybridized to an miRNA Bioarray in a water bath for 12-16 hours at 42° C. The Bioarray slides are then washed once for 60 seconds at 25° C. in Low Stringency Wash (376 ml nuclease free water+4 ml Detergent Concentrate Buffer+ 20 ml Salt Concentrate Buffer) and twice for 60 seconds at 25° C. in High Stringency Wash (780 ml nuclease free water+ 20 ml Salt Concentrate Buffer). Slides are then spun dry for 3 minutes, scanned on Agilent G2565 Microarray Scanner, and analyzed with Codelink Feature Extraction Software.

After the miRNA hybridization procedure, the array-surface bound polynucleotides are typically washed to remove unbound nucleic acids. Washing may be performed using any convenient washing protocol, where the washing conditions are typically stringent, as described above. The hybridization of the target miRNAs to the probes is then detected using standard techniques of reading the array. Reading the resultant hybridized array may be accomplished, for example, by illuminating the array and reading the location and intensity of resulting fluorescence at each feature of the array to detect miRNA/probe binding complexes.

5.7 PCR-based Methods and Other Methods of Detecting miRNA Biomarkers

Once an miRNA that is differentially expressed (either upregulated or downregulated) between a treatment and a control sample is selected, the sequence of the miRNA can be used to prepare a corresponding oligonucleotide which as a complementary probe that can identify the miRNA biomarker sequences. This probe (or corresponding oligonucleotide) can then be used to detect the selected miRNA sequence in a sample, using any suitable assay, such as PCR-based methods, Northern blotting, a dipstick assay, and the like.

Examples of PCR methods can be found, for example, in U.S. Pat. No. 6,927,024, which is incorporated by reference herein in its entirety. Examples of RT-PCR methods can be found, for example, in U.S. Pat. No. 7,122,799, which is incorporated by reference herein in its entirety. A method of fluorescent in situ PCR is described, for example, in U.S. Pat. No. 7,186,507, which is incorporated by reference herein in its entirety.

In some embodiments, Real-Time Reverse Transcription-PCR (qRT-PCR) can be used for both the detection and quantification of RNA targets. (Bustin et al., 2005, *Clin. Sci.*, 109:365-379). Quantitative results obtained by qRT-PCR can sometimes be more informative than qualitative data, and can simplify assay standardization and quality management. Thus, in some embodiments, qRT-PCR-based assays can be useful to measure miRNA levels during cell-based assays. The qRT-PCR method may be also useful in monitoring patient therapy. Examples of qRT-PCR-based methods can be found, for example, in U.S. Pat. No. 7,101,663, which is incorporated by reference herein in its entirety. Commercially available qRT-PCR based methods (e.g., TaqmanR Array™ Human miRNA panel from Applied Biosystems) may also be employed. Exemplary description of how these methods can be used to quantitate changes in miRNA levels after administration of an immunomodulatory compound is provided herein elsewhere.

5.8 Screening for Immunomodulatory Compounds using miRNA Biomarkers

In some embodiments, a method of screening for drug candidates effective in treating a disease can be obtained using the methods provided herein. At least one miRNA can be selected which has an altered (increased or decreased) expression upon effective treatment of a disease. A cell is contacted with a drug candidate. The level of miRNA is measured and compared to a similar untreated cell. The miRNA levels are analyzed to determine whether the miRNA biomarker exhibits the altered expression. Drug candidates that exhibit the altered expression pattern can then be chosen for further studies to elucidate the activity of the candidate compound.

Drug candidates for several types of disease can be screened using miRNA biomarkers. In one embodiment, the drug candidates are anti-cancer drug candidates, and the disease to be treated is cancer. In some embodiments, the drug candidates are anti-infectious disease drug candidates, and the disease to be treated is an infectious disease. The drug candidates can also be anti-viral drug candidates, and the disease to be treated is a viral infection. In further embodiments, the drug candidates are anti-bacterial drug candidates, and the disease to be treated is a bacterial infection. The screening methods described herein can also be combined with other types of drug screening methods.

5.9 Determining the Effectiveness of an Immunomodulatory Compound in a Patient using an miRNA Biomarker In some embodiments, the altered expression of at least one miRNA can be used to determine the effectiveness of the administration of an immunomodulatory compound on the treatment of a disease. At least one miRNA can be selected which has been shown to have an altered (increased or decreased) expression upon effective treatment of a disease. The miRNA can be, for example, at least one miRNA selected from miR-130a, miR-146b, miR-143, miR-145, miR-99b, miR-125a, miR-204, miR-424, and miR-503. A sample is taken from the patient, and the level of miRNA is measured and compared to that of a cell that is not being effectively treated. In some embodiments, the level of miRNA can be compared to a sample from the patient prior to treatment. In another embodiment, the level of miRNA can be compared to sample taken from a population of individuals. The miRNA levels are analyzed to determine whether the miRNA biomarker exhibits altered expression. An altered expression can indicate that the particular treatment is effective in the patient. Alternatively, a lack of change in the miRNA marker expression may indicate that the patient is not being effectively treated, or that a different treatment protocol may need to be used on the patient. Drug candidates that exhibit the altered expression pattern can then be chosen for further studies to elucidate the activity of the candidate compound.

The miRNA biomarkers provided herein can be used to determine the effectiveness of the administration of an immunomodulatory compound during patient treatment of various diseases, such as cancer, an immunological disorder, a viral infection, a fungal infection, a protozoal infection, a bacterial infection, or other diseases.

Further embodiments include assessing the effectiveness of a cancer treatment in a patient, by obtaining a patient sample, measuring the level of at least one miRNA selected from miR-130a, miR-146b, miR-143, miR-145, miR-99b, miR-125a, miR-204, miR-424, and miR-503 in the sample, and determining if the miRNA is present at an increased level in said biological sample compared to the miRNA level prior to the cancer treatment, wherein an increased miRNA level indicates the effectiveness of the cancer treatment. Examples of cancer include, but are not limited to, skin cancer, melanoma; lymph node cancer; breast cancer; cervical cancer; uterine cancer; gastrointestinal cancer; lung cancer; ovarian cancer; prostate cancer; colon cancer; rectal cancer; mouth cancer; brain cancer; head and neck cancer; throat cancer; testicular cancer; kidney cancer; pancreas cancer; bone cancer; spleen cancer; liver cancer; bladder cancer; larynx cancer; nasal passage cancer; AIDS-related cancer, blood and bone marrow cancer, multiple myeloma, acute leukemia, chronic leukemia, lymphoblastic leukemia, myelogenous leukemia, lymphocytic leukemia, myelocytic leukemias, and myelodysplastic syndrome, 5q minus syndrome, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, prostate cancer, papillary thyroid carcinoma, follicular thyroid carcinoma, medullary thyroid carcinoma, leiomyoma, and the like.

Any suitable sample can be used to assess the miRNA biomarkers. In some embodiments, the biological sample is whole blood, partially purified blood, a PBMC, a tissue biopsy, an RNA extract, a cell extract, a cell lysate, a cell, a cell culture, a cell line, a tissue, an oral tissue, a gastrointestinal tissue, an organ, an organelle, a biological fluid, a blood sample, a serum sample, a urine sample, a skin sample, a plurality of samples from a clinical trial, or the like. The sample can be a crude sample, or can be purified to various degrees prior to storage, processing, or measurement.

Samples for miRNA assessment of treatment effectiveness can be taken during any desired intervals. For example, samples can be taken hourly, twice per day, daily, weekly, monthly, every other month, yearly, or the like. The sample can be tested immediately, or can be stored for later testing.

The samples can be purified prior to testing. In some embodiments, the miRNA can be isolated from the remaining cell contents prior to testing. Further, the miRNA molecules can be separated from the rest of the mRNA in the sample, if desired. For example, because the miRNA molecules have a smaller size than mRNA molecules, the miRNA can be separated from the mRNA based on size differences prior to testing.

Control samples can be taken from various sources. In some embodiments, control samples are taken from the patient prior to treatment or prior to the presence of the disease (such as an archival blood sample). In other embodiments, the control samples are taken from a set of normal, non-diseased members of a population. A cell assay can utilize a control cell culture, for example, that has not been treated with the test compound.

miRNA-based biomarkers can also be used to track individual cells or cell cultures using cell-based assays. Cell function, effectiveness of a cell treatment, altered gene expression, and the like can be determined by use of miRNA-based biomarkers provided herein. miRNA-based biomarkers can be used to track tissues during a disease treatment with an immunomodulatory agent. For example, altered gene expression and altered cell function can be examined.

miRNA-based biomarkers can also be used to track and adjust individual patient treatment effectiveness over time. miRNA-based biomarkers can be used to gather information needed to make adjustments in a patient's treatment, increasing or decreasing the dose of an agent as needed. For example, a patient receiving an immunomodulatory agent can be tested using the miRNA-based biomarkers to see if the dosage is becoming effective, or if a more aggressive treatment plan needs to be put into place.

5.10 Optimizing Dosing of Immunomodulatory Compounds using an miRNA Biomarker The miRNA biomarkers can also be used to optimize dosing regimens of immunomodulatory compounds. Patients may respond differently to a given immunomodulatory compound, depending on such factors as age, health, genetic background, presence of other complications, disease progression, and the co-administration of other drugs. It may be useful to utilize an miRNA biomarker to assess and optimize the dosage regimen, such as the dose amount and/or the dose schedule, of an immunomodulatory compound in a patient. For example, a patient can be administered a dose of the immunomodulatory compound for a certain time, while following the level of a given miRNA known to have altered expression in patients being effectively treated. The drug can then be increased or decreased depending on the miRNA biomarker measurement. The timing of administration can also be changed upon reviewing the miRNA biomarker expression level of the patient. For example, if the miRNA expression level in a patient receiving an immunomodulatory compound appears to be unstable over time, administration frequency can be shortened, such as from once every week to once or twice per day. Further, if the level of miRNA biomarker appears to be high, the dosage of the immunomodulatory compound can then be lessened in some situations.

The miRNA biomarkers can also be used to assess and optimize the dosing over a long period of time, such as, for example, several months or years of progression of a disease. By following the biomarker levels, the dosing of the immunomodulatory compound can be changed as needed as the patient health changes.

5.11 Monitoring Treatment using miRNA Biomarkers

Also provided herein are methods of miRNA-based monitoring of the treatment and/or prevention of various disorders while the patient is being treated by administration of immunomodulatory compounds as described herein. Any suitable method of administration can be utilized. In some embodiments, the treatment involves oral or parenteral administration of the immunomodulatory agent.

The miRNA biomarkers provided herein can be used to monitor or manage immunomodulatory activity during patient treatment of various diseases, such as cancer, an immunological disorder, a viral infection, a fungal infection, a protozoal infection, a bacterial infection, or other diseases.

In some embodiments, a method of assessing or monitoring the activity of an immunomodulatory compound (e.g., presence or extent of a treatment by an immunomodulatory compound) in a patient is provided. The method generally involves selecting at least one miRNA having a level of expression that is increased or decreased in a cell treated with the immunomodulatory compound, as compared to the level of expression without the treatment. A sample is obtained from the patient, and the selected miRNA level is measured to determine whether it is present at an increased or decreased level compared to the level prior to the initiation of treatment. By following the miRNA level, the activity of an immunomodulatory compound can be monitored over time.

In some embodiments, the immunomodulatory compound can be, for example, N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; 1-oxo-2-(2,6-dioxopiperidin-3-yl)-4-aminoisoindoline; 1,3-dioxo-2-(2,6-dioxopiperidin-3-yl)-4-aminoisoindoline; 1-oxo-2-(2,6-dioxopiperidin-3-yl)-4-methylisoindoline; or N-[2-(2,6-Dioxo-piperidin-3-yl)-1,3-dioxo-2,3-dihydro-1H-isoindol-5-ylmethyl]-4-trifluoromethoxybenzamide.

In another embodiment, a method of assessing the activity of an immunomodulatory compound in a patient that is undergoing treatment with the immunomodulatory agent 1,3-dioxo-2-(2,6-dioxopiperidin-3-yl)-4-aminoisoindoline is provided. The method typically involves obtaining biological sample from the patient, measuring the level of at least one miRNA selected from miR-130a, miR-146b, miR-143, miR-145, miR-99b, miR-125a, miR-204, miR-424, and miR-503 in the sample, and determining if the miRNA is present at an increased level in the sample compared to the miRNA level prior to treatment. An increased level of at least one of these miRNA biomarkers can indicate the presence or the extent of the treatment by the immunomodulatory compound.

In some embodiments, the biomarker can be other biomarkers selected by one of skill in the art, using methods described herein.

Any suitable sample can be used to assess the miRNA biomarkers. In some embodiments, the biological sample is whole blood, partially purified blood, a PBMC, a tissue biopsy, an RNA extract, a cell extract, a cell lysate, a cell, a cell culture, a cell line, a tissue, an oral tissue, a gastrointestinal tissue, an organ, an organelle, a biological fluid, a blood sample, a serum sample, a urine sample, a skin sample, a plurality of samples from a clinical trial, or the like. The sample can be a crude sample, or can be purified to various degrees prior to storage, processing, or measurement.

Samples for miRNA assessment can be taken during any desired intervals. For example, samples can be taken hourly, twice per day, daily, weekly, monthly, every other month, yearly, or the like. The sample can be tested immediately, or can be stored for later testing.

The samples can be purified prior to testing. In some embodiments, the miRNA can be isolated from the remaining cell contents prior to testing. Further, the miRNA molecules can be separated from the rest of the mRNA in the sample, if desired. For example, because the miRNA molecules have a smaller size than mRNA molecules, the miRNA can be separated from the mRNA based on size differences prior to testing.

Control samples can be taken from various sources. In some embodiments, control samples are taken from the patient prior to treatment or prior to the presence of the disease (such as an archival blood sample). In other embodiments, the control samples are taken from a set of normal, non-diseased members of a population. A cell assay can utilize a control cell culture, for example, that has not been treated with the test compound.

miRNA-based biomarkers can be used to track patient compliance during individual treatment regimes, or during clinical trials. For example, an miRNA can be selected that is upregulated upon the administration of a given immunomodulatory drug. This can be followed at set intervals to ensure that the patients included in the trial are taking the drugs as instructed. Further, a patient receiving an immunomodulatory agent can be tested using the miRNA-based biomarkers to determine whether the patient complies with the dosing regimen of the treatment plan.

In some embodiments, a method for assessing patient compliance with a drug treatment protocol is provided. The method can involve, for example, selecting at least one miRNA biomarker that has an altered expression level in response to a drug treatment protocol. Preferably, the miRNA is at least one of miR-130a, miR-146b, miR-143, miR-145, miR-99b, miR-125a, miR-204, miR-424, or miR-503. A biological sample is obtained from the patient, and the miRNA biomarker level is measured and compared to that of a control untreated sample. An altered expression level of the biomarker compared to that of an untreated control sample indicates compliance with the protocol.

For example, when at least one of miR-130a, miR-146b, miR-143, or miR-145, miR-99b, miR-125a, miR-204, miR-424, or miR-503 is measured, an increased level of the biomarker compared to that of an untreated control indicates at least partial patient compliance with the drug treatment protocol. An increased level of the biomarker that is at a similar quantity to that of a positive control indicates the likelihood of full compliance with the treatment protocol. Example 6.13, 6.15 and 6.18 provide descriptions of the use of miRNA biomarkers to perform this type of compliance testing.

5.12 Kits for Detecting miRNA Biomarkers

In some embodiments, a kit for detecting immunomodulatory compound-induced differentially expressed miRNAs can be prepared. The kits can include, for example, a probe or probe set comprising oligonucleotides that can bind to the miRNA biomarker(s) of interest for a given disease, compound, or other parameter. Washing solutions, reagents for performing a hybridization assay, miRNA isolation or purification means, detection means, as well as positive and negative controls can also be included. The kit can also include instructions for using the components of the kit. The kit can be tailored for in-home use, clinical use, or research use. An example of the preparation of a test strip suitable for such a kit is disclosed in Example 6.12.

5.13 Administration of Immunomodulatory Compound to Increase the Expression Level of miRNA Biomarkers Certain miRNAs are involved in important regulatory processes in the cell. Thus, the ability to upregulate or downregulate these miRNAs as needed can be an important tool in treating many types of diseases. Accordingly, in some embodiments, immunomodulatory compounds described herein can be administered to a cell to alter the level of an miRNA biomarker in the cell. Additionally, immunomodulatory compounds described herein can be administered to a patient in an amount effective to alter the level of a miRNA biomarker in a biological sample taken from the patient.

In some embodiments, the biomarker is selected from at least one of the following: miR-130a, miR-146b, miR-143, miR-145, miR-99b, miR-125a, miR-204, miR-424, and miR-503. The biomarker may also be another selected miRNA sequence. In some embodiments, the biomarker is upregulated. In other embodiments, the biomarker is downregulated.

All of the references cited herein are incorporated in their entireties by reference. The following examples are offered for illustrative purposes only, and are not intended to limit the scope of the present invention in any way.

6. EXAMPLES

6.1 Preparation of Cd34$^+$ Cells

A CD34$^+$ hematopoietic precursor cell line was utilized to examine miRNA biomarker expression upon treatment with an immunomodulatory compound. CD34$^+$ cells used in preclinical studies were purchased from a commercial supplier (Lonza), isolated by positive immunomagnetic selection from bone marrow. In clinical studies, CD34$^+$ cells can be purified by positive immunomagnetic selection or by flow cytometric immunosorting from bone marrow or peripheral blood using conventional methodologies.

6.2 Administration of 1,3-dioxo-2-(2,6-dioxopiperidin-3-yl)-4-aminoisoindoline to CD34$^+$ cells CD34$^+$ cells were expanded for 6 days in Iscove's DMEM media (Invitrogen) with 20% BIT serum substitute (StemCell Technologies) in the presence of SCF (100 ng/ml), Flt-3 ligand (100 ng/ml), and IL-3 (20 ng/ml) and then differentiated for 6 days in Iscove's/20% BIT containing SCF (50 ng/ml) and erythropoietin (2 U/ml) in the presence of 0.1% DMSO, 1 or 10 uM the immunomodulatory compound. Cells were grown in tissue culture and treated with the immunomodulatory compound according to methods known in the art.

6.3 Differential Expression Profiling Method

To detect whether certain miRNAs were expressed after treatment with the immunomodulatory compound 1,3-dioxo-2-(2,6-dioxopiperidin-3-yl)-4-aminoisoindoline, RNA expression profiling was initially performed to compare treated and untreated cells. An miRNA fraction was purified from immunomodulatory compound treated cells using the mirVana™ miRNA Isolation Kit (Ambion). One skilled in the art can emulate this methodology in general terms by first purifying total RNA from cells with a single acid-phenol (pH 5.0) extraction and then sequentially enriching mRNA and miRNA fractions by binding to a nucleic acid binding matrix under conditions that favor the binding of large RNAs (20% EtOH) and small RNA (70% EtOH), respectively. One to two vtg of purified miRNA was then end-labeled with Cy5™ using the mirVana™ miRNA Labeling Kit (Ambion). Alternatively, this enzymatic labeling can be accomplished with miRNA, poly (A) polymerase, MnCl2, amine modified NTP, and Cy5 NHS-ester (Amersham) under the appropriate buffer conditions at 37° C. Cy5 labeled miRNA was hybridized to miRNA Bioarrays (Ambion) and washed according to manufacturer's instructions.

The expression array method detected two miRNAs that were regulated by administration of immunomodulatory agents in the CD34$^+$ hematopoietic precursor model. The miRNAs miR-146b (FIG. 1A) and miR-130a (FIG. 1B) were upregulated upon administration of 1,3-dioxo-2-(2,6-dioxopiperidin-3-yl)-4-aminoisoindoline.

6.4 Example of qRT-PCR Method Used to Quantitate Selected miRNA Biomarkers in Sample To quantitate selected miRNAs with qRT-PCR, purified miRNA was analyzed using a TaqmanR microRNA Assay (Applied Biosystems). Five ng of purified miRNA was subjected to qRT-PCR with TaqmanR miRNA assay according to manufacturers instructions. Alternatively, the procedure may be achieved by using miRNA-specific reverse transcription and PCR primers with standard buffers, reagents, and methods.

Figure 1B:
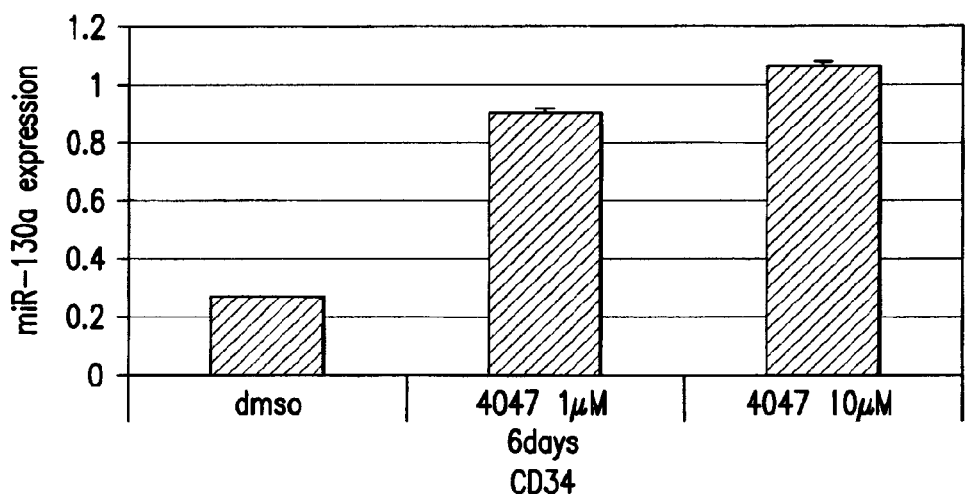
FIG. 1B is a bar graph illustrating miR-130a expression as measured by qRT-PCR in CD34 cells expanded and differentiated with Epo for 6 days in the presence of 0.1% DMSO or 1,3-dioxo-2-(2,6-dioxopiperidin-3-yl)-4-aminoisoindoline (1 or 10 µM).

6.5 Use of biomarkers miR-130a and miR-146b to test CD34$^+$ cell cultures treated with 1,3-dioxo-2-(2,6-dioxopiperidin-3-yl)-4-aminoisoindoline Levels of miR-130a and miR-146b were determined using qRT-PCR as described above. FIG. 1A shows the upregulation of miR-146b expression after 6 days of cell culture growth in either 1 or 10 µm 1,3-dioxo-2-(2,6-dioxopiperidin-3-yl)-4-aminoisoindoline, compared to the DMSO control. Similarly, FIG. 1B shows the upregulation of miR-130a expression after 6 days of cell culture growth in either 1 or 10 µm 1,3-dioxo-2-(2,6-dioxopiperidin-3-yl)-4-aminoisoindoline, compared to the DMSO control.

6.6 Preparation of Namalwa Cells

An experiment similar to described above in Sections 6.1-6.5 was performed with a Namalwa lymphoma cell line model. The Namalwa Burkitt's lymphoma cell line was purchased from ATCC and grown in RPMI with 10% fetal bovine serum according to standard tissue culture methods known in the art.

6.7 Administration of 1,3-dioxo-2-(2,6-dioxopiperidin-3-yl)-4-aminoisoindoline to Namalwa cells Namalwa cells grown as above were treated for 6 or 24 hours with either 0.1% DMSO, 10 µM 1,3-dioxo-2-(2,6-dioxopiperidin-3-yl)-4-aminoisoindoline, or the HDAC inhibitor TSA 1 µM. Cells were harvested at indicated times and then miRNA was purified as outlined in previous sections.

6.8 miRNA expression profile of 1,3-dioxo-2-(2,6-dioxopiperidin-3-yl)-4-aminoisoindoline-treated Namalwa cells and selection of biomarkers miR-145 and miR-143 miRNA expression profiles in Namalwa cells treated with immunomodulatory compounds were generated using methods similar to that described in Section 6.3.

Figure 2A:
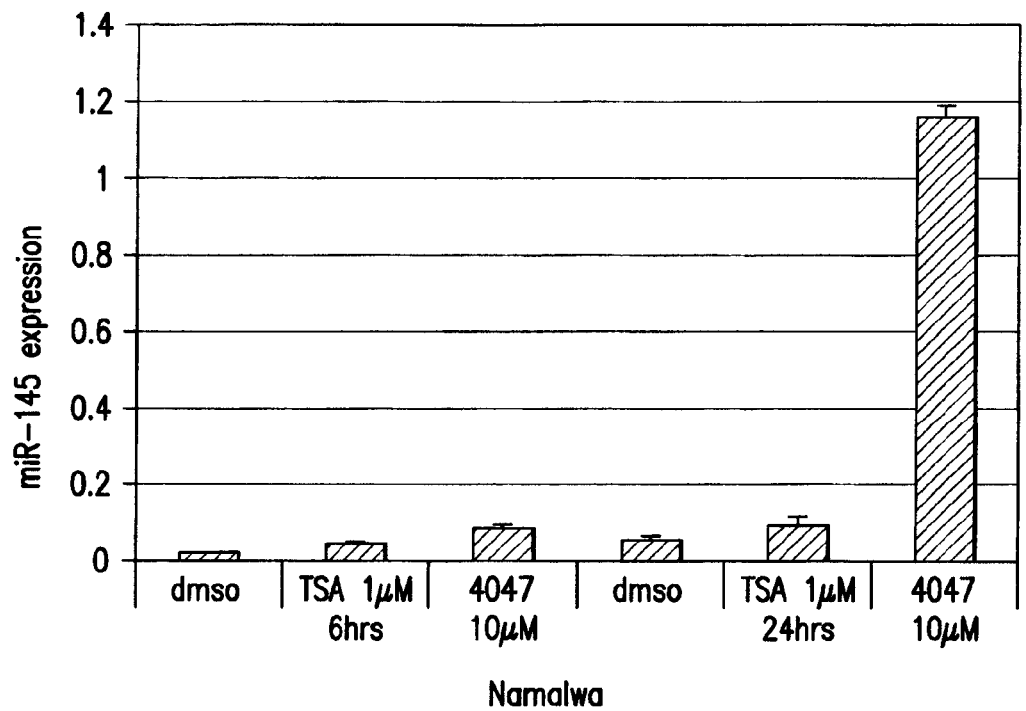
FIG. 2A is a bar graph illustrating miR-145 expression measured by qRT-PCR in Namalwa cells treated for 6 or 24 hours with either DMSO (0.1%), 1,3-dioxo-2-(2,6-dioxopiperidin-3-yl)-4-aminoisoindoline (10 µM), or the histone deacetylase (HDAC) inhibitor Trichostatin A (TSA) (1 µM).
Figure 2B:
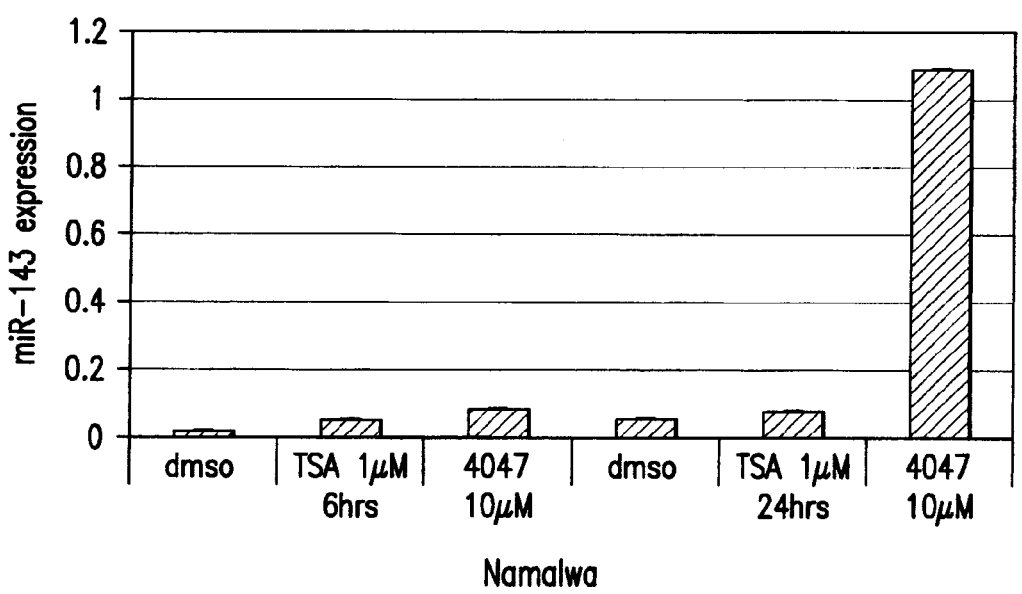
FIG. 2B is a bar graph illustrating miR-143 expression measured by qRT-PCR in Namalwa cells treated for 6 or 24 hours with either DMSO (0.1%), 1,3-dioxo-2-(2,6-dioxopiperidin-3-yl)-4-aminoisoindoline (10 µM), or the HDAC inhibitor TSA (1 µM).

Treatment of Namalwa cells with 1,3-dioxo-2-(2,6-dioxopiperidin-3-yl)-4-aminoisoindoline resulted in the upregulation of the miRNAs miR-143 and miR-145, as shown in FIG. 2. The miRNAs miR-143 and miR-145 have been found to map to chromosome 5q33, a region deleted in about 30% of MDS patients. This region is thought to harbor genes that enhance lenalidomide sensitivity. These two miRNAs, miR-143 and miR-145, are also expressed at low levels in colon and breast cancers and B-cell lymphoma as compared to normal tissue. Thus, miR-143 and miR-145 may act as tumor suppressors, and may mediate lenalidomide sensitivity in 5q-minus cell lines such as Namalwa cell lines. They may also mediate lenalidomide sensitivity in MDS. Further, miR-143 and miR-145 may be involved in the mechanism of action of the immunomodulatory compound.

6.9 Use of biomarkers miR-145 and miR-143 to test cell samples treated with 1,3-dioxo-2-(2,6-dioxopiperidin-3-yl)-4-aminoisoindoline Levels of miR-145 and miR-143 were determined using qRT-PCR. Purified miRNA was analyzed using a TaqmanR microRNA expression assay (Applied Biosystems). Five ng of purified miRNA was subjected to qRT-PCR with TaqmanR miRNA assays for miR-143 and miR-145 according to manufacturers instructions. The procedure may be achieved by using miRNA reverse transcription and PCR primers with standard buffers, reagents, and methods.

6.10 Determination of miRNA biomarkers in cell cultures treated with 1-oxo-2-(2,6-dioxopiperidin-3-yl)-4-aminoisoindoline Additional assays were performed to determine the effects of lenalidomide (1-oxo-2-(2,6-dioxopiperidin-3-yl)-4-aminoisoindoline) administration to various cell cultures on the expression of miRNAs. The miRNAs were detected using the Agilent miRNA array v2, which contains probes for 760 human miRNAs. Total mRNA was isolated using the Qiagen miRNeasy kit, total RNA (100 ng) was dephosphorylated and ligated with pCp-Cy3. Labeled RNA was purified and hybridized to Agilent miRNA arrays.

Namalwa cells: Lenalidomide was added to Namalwa cells at a concentration of 0.1 µm, 1 µm, or 10 µm. The miRNA levels were measured at 24 and 48 hours after addition of the lenalidomide. The results with this array confirmed the upregulation of miR-143 and miR-145 in Namalwa cells in a dose-dependent response to administration of 1-oxo-2-(2,6-dioxopiperidin-3-yl)-4-aminoisoindoline (Table 2).

TABLE 2 miRNAs Modulated by Lenalidomide in Namalwa Cells

| | 24 hour treatment (Fold Increase) | | | 48 hour treatment (Fold Increase) | |
|---|---|---|---|---|---|
| | 0.1 uM lenalidomide | 1 uM lenalidomide | 10 uM lenalidomide | 0.1 uM lenalidomide | 1 uM lenalidomide |
| miR-145 | 2.34 | 4.16 | 4.96 | 2.53 | 5.12 |
| miR-143 | 2.29 | 3.81 | 4.69 | 2.31 | 4.68 |

HL60 cells: The addition of lenalidomide (1-oxo-2-(2,6-dioxopiperidin-3-yl)-4-aminoisoindoline) to a cell culture from an acute myelogenous leukemia (AML) cell line (HL60) was also shown to upregulate a number of miRNAs. The upregulated miRNA included miR-143 and miR-145. In addition, the miRNAs miR-146b, miR-99b, and miR-125a were also upregulated by 1-oxo-2-(2,6-dioxopiperidin-3-yl)-4-aminoisoindoline in a dose dependent manner at both 24 and 48 hours (Table 3).

TABLE 3 miRNAs Modulated by Lenalidomide in HL-60 Cells

| | 24 hour treatment (Fold Increase) | | | 48 hour treatment (Fold Increase) | | |
|---|---|---|---|---|---|---|
| | Lenalidomide conc (uM) | | | | | |
| | 0.1 | 1.0 | 10.0 | 0.1 | 1.0 | 10.0 |
| miR-146b | 2.28 | 2.99 | 3.29 | 4.38 | 7.16 | 7.07 |
| miR-99b | 1.81 | 2.37 | 2.53 | 1.99 | 2.45 | 2.69 |
| miR-145 | 1.33 | 1.62 | 1.77 | 1.89 | 2.27 | 2.34 |
| miR-125a | 1.56 | 1.93 | 2.04 | 1.72 | 2.05 | 2.24 |
| miR-143 | 1.42 | 1.56 | 1.63 | 1.96 | 2.40 | 2.25 |

H929 cells: Cells from the multiple myeloma cell line H929 were treated with lenalidomide (1-oxo-2-(2,6-dioxopiperidin-3-yl)-4-aminoisoindoline) for 24 and 48 hours. miRNAs were then identified which exhibited an increase in expression in a dose dependent manner. The identified miRNAs were miR-204, miR-424, and miR-503, as shown in Table 4 below.

TABLE 4 miRNAs modulated by lenalidomide in H929 cells

| | 24 hour treatment (Fold Increase) | | | 48 hour treatment (Fold Increase) | | |
|---|---|---|---|---|---|---|
| | Lenalidomide conc (uM) | | | | | |
| | 0.1 | 1.0 | 10.0 | 0.1 | 1.0 | 10.0 |
| miR-204 | 1.75 | 2.20 | 2.00 | 2.61 | 4.30 | 4.45 |
| miR-424 | 1.50 | 2.08 | 2.10 | 1.71 | 3.08 | 3.36 |
| miR-503 | 1.61 | 2.37 | 2.44 | 1.89 | 3.80 | 4.05 |

6.11 Selection and Use of Biomarkers to Follow Patient Treatment with an Immunomodulatory Compound for Pain Relating to an Immunological Disorder A study is performed to evaluate the patient compliance of oral administration of an immunomodulatory compound described herein. Patients receive the compound in an amount of 100 mg/d or 300 mg/d daily, in tablet form, to be self-administered orally. To measure patient compliance, an miRNA biomarker that is expressed when a particular immunomodulatory compound is administered to the patient is selected. One ml blood samples are taken 2 times per week, and the level of the two selected miRNA biomarkers is measured. The percentage of compliance is tracked over time. The study further monitors patient's self-assessment of pain level, hematological tests, serum chemistries, urinalysis, adverse events, urine or serum pregnancy tests, vital signs, ECG and physical examinations. By use of this method, compliance with the trial protocol can be measured.

6.12 Selection and Use of Biomarkers to Follow Patient Treatment for MDS

A study is performed to monitor the patient compliance of the oral administration of an immunomodulatory compound in patients with MDS. Patients receive the therapy in 4-week cycles for 16 weeks (4 cycles) or 24 weeks (6 cycles). The subject population comprises patients with low- or intermediate-1-risk MDS (International Prognostic Scoring System) with red blood cell transfusion-dependent anemia who have received at least two units of RBCs within 8 week of baseline (first day of study treatment).

Using cell-based assays on cells derived from patients, separate miRNA biomarkers are selected which can confirm that the drug has, indeed, been administered (patient compliance). The miRNA biomarker-based measurements of patient administration compliance is performed following procedures similar to those described in Section 6.10, above. By use of this method, compliance with the trial protocol can be measured monitored.

All of the references cited herein are incorporated by reference in their entirety. While the invention has been described with respect to the particular embodiments, it will be apparent to those skilled in the art that various changes and modifications may be made without departing from the spirit and scope of the invention as recited by the appended claims.

The embodiments provided herein described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method for identifying an immunomodulatory compound, comprising:
   a) obtaining a biological sample from a patient;
   b) contacting a cancer cell from the biological sample with the compound;
   c) detecting the presence of a miRNA expression, wherein the miRNA is miR-143, or miR-145 in the cancer cell;
   d) quantifying the level of expression of the miRNA in the cancer cell and the level of the same miRNA in a cell not contacted with the compound; and
   e) assessing the difference in the level of the miRNA expression in the cancer cell contacted with the compound and in the cell not contacted with the compound to identify the immunomodulatory compound, wherein an increased level of expression of one or more of the miRNA correlates with an immunomodulatory activity.

2. The method of claim 1, wherein the increased level of expression of one or more of the miRNA correlates with the compound's efficacy in treating cancer.

* * * * *